United States Patent [19]

Donald et al.

[11] Patent Number: 5,296,489

[45] Date of Patent: Mar. 22, 1994

[54] IMMUNOSUPPRESSIVE MACROCYCLIC COMPOUNDS

[75] Inventors: David K. Donald, Ashby-de-la-Zouch; Mark Furber, Derby; Martin E. Cooper, Leicestershire, all of England

[73] Assignee: FISONS, Ipswich, England

[21] Appl. No.: 924,067

[22] PCT Filed: Mar. 13, 1991

[86] PCT No.: PCT/GB91/00393

§ 371 Date: Sep. 11, 1992

§ 102(e) Date: Sep. 11, 1992

[87] PCT Pub. No.: WO91/13889

PCT Pub. Date: Sep. 19, 1991

[30] Foreign Application Priority Data

| Mar. 13, 1990 | [GB] | United Kingdom | 90/05672 |
| Apr. 17, 1990 | [GB] | United Kingdom | 90/08507 |
| Apr. 17, 1990 | [GB] | United Kingdom | 90/08556 |
| Apr. 27, 1990 | [GB] | United Kingdom | 90/09480 |
| Aug. 9, 1990 | [GB] | United Kingdom | 90/17447 |
| Oct. 25, 1990 | [GB] | United Kingdom | 90/23242 |

[51] Int. Cl.$^5$ ............... C07D 498/18; A61K 31/395

[52] U.S. Cl. ................... 514/291; 514/411; 540/456

[58] Field of Search ............... 540/456; 514/291, 411

[56] References Cited

FOREIGN PATENT DOCUMENTS

| 0184162 | 6/1986 | European Pat. Off. | 540/456 |
| 0323042 | 7/1989 | European Pat. Off. | 540/456 |
| 0356399 | 2/1990 | European Pat. Off. | 540/456 |

*Primary Examiner*—Robert T. Bond
*Attorney, Agent, or Firm*—Marshall, O'Toole, Gerstein, Murray & Borun

[57] ABSTRACT

There are provided compounds of formula (I), wherein $R^1$ represents H, OH or alkoxy; $R^2$ represents H; in addition $R^1$ and $R^2$ may together represent a second bond between the carbon atoms to which they are attached; $R^3$ represents methyl, ethyl, propyl or allyl; $R^4$ represents H, OH, alkyl, alkoxy, halogen, amino, S-alkyl, NHCHO or NHCO-alkyl; n represents 1 or 2; X represents O, (H, OH), (H, H) or =NH; and Y represents an optionally substituted cyclohexyl or substituted cyclopentyl group; with various provisos. The compounds are useful, inter alia, as immunosuppressive agents.

9 Claims, No Drawings

IMMUNOSUPPRESSIVE MACROCYCLIC COMPOUNDS

This invention relates to immunosuppressive macrocyclic compounds, processes for their preparation, their use as medicaments, and compositions containing them.

European Patent Application 184162 (to Fujisawa Pharmaceuticals Co Ltd) discloses a number of macrocyclic compounds isolated from microorganisms belonging to the genus Streptomyces. The macrolides are numbered FR-900506, FR-900520, FR-900523 and FR-900525, and the preparation of some of their derivatives is also described.

International Patent Applications Nos WO 89/05304 and PCT/GB90/01262 and European Patent Application No 413532 (to Fisons plc), European Patent Application 353678 (to Fujisawa Pharmaceuticals CO Ltd), European Patent Applications 349049, 349061, 358508 and 388153 (to Merck & CO Inc) and European Patent Application 356399 and International Patent Application WO 90/15805 (to Sandoz AG) also disclose a number of immunosuppressive macrocyclic compounds.

We have now found a new group of immunosuppressive macrocyclic compounds which possess advantageous properties over those disclosed previously.

According to the present invention, there is provided a compound of formula I,

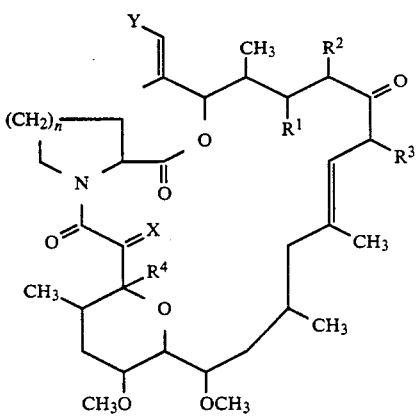

wherein
$R^1$ represents H, OH or alkoxy;
$R^2$ represents H;
in addition, $R^1$ and $R^2$ may together represent a second bond between the carbon atoms to which they are attached;
$R^3$ represents methyl, ethyl, propyl or allyl;
$R^4$ represents H, OH, alkyl, alkoxy, halogen, amino, S-alkyl, NHCHO or NHCO-alkyl;
n represents 1 or 2;
X represents O, (H,OH), (H,H) or =NH; and
Y represents a cyclic group of formula II,

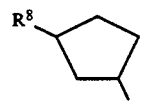

in which $R^5$ represents (H,H), (H,OH), (H,methoxy) or O;

$R^6$ represents H, (R)—OH, (S)—OH, alkoxy, amino, alkylazino, alkanoylamino, formyloxy or halogen; $R^7$ represents H; and in addition $R^5$ and $R^6$ may together represent a second bond between the carbon atoms to which they are attached; or $R^6$ and $R^7$ may together represent a second bond between the carbon atoms to which they are attached;
or a cyclic group of formula III,

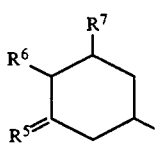

in which $R^8$ represents alkyl substituted by one or more groups selected from OH, alkoxy, =O, and $CO_2H$; or alkenyl optionally substituted by one or more groups selected from OH, =O, or $CO_2H$;
provided that
a) when n represents 1; $R^1$ represents OH; $R^3$ represents allyl; $R^4$ represents OH; $R^5$ represents (H,methoxy); and $R^6$ represents (R)—OH; then X does not represent O;
b) when n represents 2;
i) $R^1$ represents OH; $R^3$ represents methyl, ethyl, allyl or propyl; $R^4$ represents OH; $R^5$ represents (H,methoxy); and $R^6$ represents (R)—OH; then X does not represent O;
ii) when $R^1$ and $R^2$ together represent a second bond between the carbon atoms to which they are attached or each represent H; $R^3$ represents allyl or propyl; $R^4$ represents OH; $R^5$ represents (H,methoxy); and $R^6$ represents (R)—OH; then X does not represent O;
iii) when $R^1$ represents OH, methoxy or together with $R^2$ it represents a second bond between the carbon atoms to which they are attached; $R^3$ represents allyl; $R^4$ represents OH; $R^5$ represents (H,methoxy); and $R^6$ represents methoxy; then X does not represent O;
iv) when $R^1$ represents H or OH; $R^3$ represents allyl; $R^4$ represents OH; $R^5$ represents (H,methoxy); and $R^6$ represents (R)—OH; then X does not represent (H,OH);
v) when $R^1$ represents H; $R^3$ represents propyl; $R^4$ represents OH; $R^5$ represents (H,OH); and $R^6$ represents (R)—OH; then X does not represent O;
vi) when $R^1$ represents OH; $R^3$ represents ethyl; $R^4$ represents OH; $R^5$ represents (H,methoxy); and $R^6$ represents (R)—OH; then X does not represent (H,OH);
vii) when $R^1$ and $R^2$ together represent a second bond between the carbon atoms to which they are attached or each represent H; $R^3$ represents ethyl; $R^4$ represents OH; $R^5$ represents (H,methoxy); and $R^6$ represents (R)—OH; then X does not represent O;
viii) when $R^1$ represents OH; $R^3$ represents allyl; $R^4$ represents OH; $R^5$ represents (H,OH) or (H,methoxy); and $R^6$ represents (R)—OH; then X does not represent (H,H);
ix) when $R^1$ represents OH; $R^3$ represents ethyl; $R^4$ represents OH; $R^5$ represents (H,methoxy); and $R^6$ represents (R)—OH; then X does not represent (H,H);
x) when $R^1$ represents OH; $R^3$ represents methyl, ethyl or allyl; $R^4$ represents OH; $R^5$ represents (H,OH); and $R^6$ represents (R)—OH; then X does not represent O; and xi) when $R^1$ represents OH; $R^3$ represents allyl; $R^4$ represents OH; $R^5$ represents O; and $R^6$ represents (R)—OH; then X does not represent O;

and pharmaceutically acceptable derivatives thereof.

Pharmaceutically acceptable derivatives which may be mentioned include esters, amides and salts of any carboxylic acid groups which may be present. The esters and amides preferably contain up to 6 carbon atoms. Salts include alkali metal and alkaline earth metal salts, for example sodium or calcium.

When any one of $R^1$, $R^4$, $R^5$, $R^6$, and $R^8$ represent carbon-containing groups, we prefer those groups to contain up to 10 carbon atoms, more preferably up to 6 carbon atoms.

Groups which $R^8$ may represent include CHO and $CO_2H$.

Preferably, $R^1$ represents H or OH. We prefer $R^4$ to represent H, OH, alkyl, halogen or amino. Desirably, $R^5$ represents (H,OH) or (H,methoxy). Preferably $R^6$ represents H, (R)—OH or amino. We prefer $R^8$ to represent an amide of a $CO_2H$ group or alkyl substituted by alkoxy.

Subgroups of compounds which may be mentioned include: compounds of formula I in which Y represents a cyclic group of formula III; compounds of formula I in which $R^4$ represents alkoxy; compounds of formula I in which $R^4$ represents amino, alkylamino, alkanoylamino, halogen and thioalkyl; compounds of formula I in which $R^4$ represents H or alkyl; and compounds of formula I in which $R^6$ represents H, (S)—OH or halogen or together with $R^5$ represents a second bond between the carbon atoms to which they are attached or together represent a pair of vicinal hydrogen atoms.

A preferred group of specific compounds which may be mentioned is:

17-allyl-1,14-dihydroxy-12-[2-(3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-allyl-1,14-dihydroxy-12-[2-(cyclopentyl-3-carboxylic acid morpholine amide)-1-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone;

17-allyl-14-hydroxy-12-(2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-allyl-14-hydroxy-12-[2-(4-hydroxy-3-methoxycyclohexyl)-1-methylvinyl)-23,25-dimethoxy-1,13,19,21,27-pentamethyl-11,28-dioxa-4-azatricyclo[22.3.1.0$^{4,9}$]octacos-18-ene-2,3,10,16-tetraone;

17-allyl-i-amino-14-hydroxy-12-[2-(4-hydroxy-3-methoxycyclo hexyl)-1-methylvinyl]-23,25-dimethoxy-13,19,21,27-tetra methyl-11,28-dioxa-4-azatricyclo[22.3.1.0$^{4,9}$]octacos-18-ene-2,3,10,16-tetraone;

17-allyl-l-fluoro-14-hydroxy-12-(2-(4-hydroxy-3-methoxycyclo hexyl)-1-methylvinyl)-23,25-dimethoxy-13,19,21,27-tetramethyl-11,28-dioxa-4-azatricyclo(22.3.1.0$^{4,9}$]octacos-18-ene-2,3,10,16-tetraone;

17-Allyl-1,14-dihydroxy-12-[2-(cyclopentyl-3-methanol(methyl ether))-1-methylvinyl]-23,25-dimethoxy-13,19,21,27-tetra methyl-11,28-dioxa-4-azatricyclo[22.3.1.0$^{4,9}$]octacos-18-ene-2,3,10,16-tetraone; and 17-Allyl-1,14-dihydroxy-12-[2-(4-amino-3-methoxycyclohexyl)-1-methylvinyl)-23,25-dimethoxy-13,19,21,27-tetramethyl-11,28-dioxa-4-azatricyclo(22.3.1.0$^{4,9}$]octacos-18-ene-2,3,10,16-tetraone.

The compounds disclosed in the above-mentioned applications may be used as starting materials for the production of compounds of the present invention. Alternatively, they may be prepared by total synthesis.

According to a further aspect of the invention, there is provided a process for the production of a compound of formula I as defined in claim 1, which comprises:

(a) producing a compound of formula I in which $R^1$ and $R^2$ together represent a second carbon-carbon bond between the carbon atoms to which they are attached, by dehydration of a corresponding compound in which $R^1$ represents OH and $R^2$ represents H;

(b) producing a compound of formula I in which $R^1$ and $R^2$ each represent hydrogen, by reduction of a corresponding compound in which $R^1$ and $R^2$ together represent a second carbon-carbon bond between the carbon atoms to which they are attached;

(c) producing a compound of formula I in which X represents (H,OH), by reduction of a corresponding compound in which X represents O;

(d) producing a compound of formula I in which X represents (H,H), by reduction of a corresponding compound in which X represents O;

(e) producing a compound of formula I in which X represents O, by oxidation of a corresponding compound in which X represents (H,OH);

(f) producing a compound of formula I in which $R^4$ represents alkoxy, by reaction of a corresponding compound in which $R^4$ represents OH and X represents (H,OH) with an alkanol;

(g) producing a compound of formula I in which $R^4$ represents halogen, by reaction of a corresponding compound in which $R^4$ represents OH with a suitable halogenating agent;

(h) producing a compound of formula I in which $R^4$ represents H or alkyl, by reaction of a corresponding compound in which $R^4$ represents halogen with an organometallic reagent;

(i) producing a compound of formula I in which $R^4$ represents amino, by reaction of a corresponding compound in which $R^4$ represents halogen with ammonia;

(j) producing a compound of formula I in which X represents =NH, by reaction of a corresponding compound in which X represents O with ammonia;

(k) producing a compound of formula I in which $R^4$ represents S-alkyl, by reaction of a corresponding compound in which $R^4$ represents halogen with an alkylthiol;

(l) producing a compound of formula I in which $R^4$ represents NHCHO, by reaction of a corresponding compound in which $R^4$ represents amino with formic acid;

(m) producing a compound of formula I in which $R^4$ represents NHCO-alkyl, by reaction of a corresponding compound in which $R^4$ represents amino with an alkanoic anhydride;

(n) producing a compound of formula I in which $R^6$ represents (S)—OH, by elimination of a leaving group from a corresponding compound in which $R^6$ represents the leaving group;

(o) producing a compound of formula I in which $R^6$ represents H and $R^5$ represents O, by elimination of a leaving group from a corresponding compound in which $R^6$ represents the leaving group;

(p) producing a compound of formula I in which $R^6$ and $R^7$ together represent a second bond between the carbon atoms to which they are attached, by elimination of a leaving group from a corresponding compound in which $R^6$ represents the leaving group;

(q) producing a compound of formula I in which Y represents a cyclic group of formula III and $R^8$ represents CHO, by elimination of a leaving group from a corresponding compound in which $R^6$ represents the leaving group;

(r) producing a compound of formula I in which $R^6$ represents halogen, by reaction of a corresponding compound in which $R^6$ represents a leaving group with halide ion;

(s) producing a compound of formula I in which $R^5$ and $R^6$ together represent a second bond between the carbon atoms to which they are attached, by elimination of halogen and alkoxy from a corresponding compound in which $R^5$ represents alkoxy and $R^6$ represents halogen;

(t) producing a compound of formula I in which $R^5$ represents (H,H) and $R^6$ represents H, by reduction of a corresponding compound in which $R^5$ and $R^6$ together represent a second bond between the carbon atoms to which they are attached;

(u) producing a compound of formula I in which $R^6$ represents H, by the action of hydride on a corresponding compound in which $R^6$ represents a leaving group;

(v) producing a compound of formula I in which $R^6$ represents amino, by reduction of a corresponding compound in which $R^6$ represents azido;

(w) producing a compound of formula I in which $R^6$ represents alkylamino or alkanoylamino, by reaction of a corresponding compound in which $R^6$ represents amino with a suitable alkylating or acylating reagent;

(x) producing a compound of formula I in which $R^8$ represents alkyl substituted by OH, by reduction of a corresponding compound in which $R^8$ represents alkyl substituted by =O;

(y) producing a compound of formula I in which $R^8$ includes a carboxylic acid group, by oxidation of a corresponding compound in which $R^8$ includes an aldehyde group; and (z) producing a compound of formula I in which $R^8$ represents optionally substituted alkenyl, by a Wittig reaction between a corresponding compound in which $R^8$ includes an aldehyde and an appropriate Wittig reagent.

In process (a), the dehydration may be carried out in a solvent which does not adversely affect the reaction (e.g. toluene), in the presence of a trace amount of acid (e.g. p-toluenesulphonic acid), at a temperature of from 50° to 100° C.

In processes (b) and (t), the reduction may be carried out catalytically using hydrogen. Suitable catalysts include platinum catalysts (e.g. platinum black, platinum oxides), palladium catalysts (e.g. palladium oxides, palladium on charcoal), nickel catalysts (e.g. nickel oxide, Raney Nickel), and rhodium catalysts (e.g. rhodium on alumina). Suitable solvents are those which do not adversely affect the reaction, and include methanol, ethanol, ethyl acetate, dichloromethane and dimethylformamide. The reduction may be carried out at or around room temperature.

In process (c), suitable reagents for the reduction include tri-$^n$butyltin hydride in a solvent which does not adversely affect the reaction (e.g. toluene) at a temperature of from 50° to 100° C., sodium borohydride, zinc in acetic acid at or around room temperature, sodium triacetoxyborohydride in acetic acid, L-Selectride (Registered Trade Mark) in tetrahydrofuran, or borane/$^t$butylamine complex in a solvent such as methanol or ethanol.

In process (d), the reduction may be achieved by the action of $H_2S$, preferably in the presence of pyridine or an amine (for example morpholine), in a solvent which does not adversely affect the reaction (for example dimethylformamide, pyridine or methanol), at or around room temperature.

In process (e), the oxidation may be carried out in the presence of a suitable oxidizing agent, such as cupric acetate. Suitable solvents include those which do not adversely affect the reaction, for example methanol. The reaction may be carried out up to the reflux temperature of the solvent.

In process (f), the reaction may be carried out in the presence of a suitable acid catalyst, for example montmorillonite K10. The solvent used may conveniently be the alkanol reagent, and the reaction may be carried out at or around room temperature.

In process (g), suitable halogenating agents include diethylaminosulphur trifluoride and thionyl chloride. The halogenation is preferably carried out in a solvent which does not adversely affect the reaction, for example dichloromethane, at or below room temperature, and preferably under an inert atmosphere.

In process (h), suitable organometallic reagents include lithium dialkyl copper reagents, which may be prepared from a copper halide and an alkyl lithium reagent. $R^4$ preferably represents Cl in the starting material. Suitable solvents include those which do not adversely affect the reaction, for example diethyl ether. The reaction is preferably carried out at reduced temperature.

In processes (i) and (j), suitable solvents include those which do not adversely affect the reaction, for example diethyl ether. $R^4$ preferably represents Cl in the starting material. The reaction may be carried out at or around room temperature.

In process (k), suitable solvents include those which do not adversely affect the reaction, for example tetrahydrofuran (THF). $R^4$ Preferably represents Cl in the starting material. The reaction may be carried out at or around room temperature.

In process (l), the solvent is conveniently formic acid. The reaction may be carried out at or around room temperature, and in the presence of acetic anhydride.

In process (m), suitable solvents include those which do not adversely affect the reaction, for example methanol. The reaction may be carried out at below room temperature.

is In processes (n)–(q), suitable leaving groups include tosylate, mesylate and triflate (trifluoromethylsulphonyloxy), and the elimination is carried out in the presence of an acid catalyst, preferably silica. The leaving group may be introduced by reaction of a compound of formula I in which $R^6$ represents (R)—OH with a suitable reagent, for example trifluoromethanesulphonic acid anhydride.

In process (r), suitable leaving groups include tosylate, mesylate and triflate. Suitable sources of halide include tetra-nbutylammonium halides, for example tetra-$^n$butylammonium iodide. Suitable solvents include those which do not adversely affect the reaction, for example benzene. The reaction may be carried out at at or around room temperature.

In process (s), the elimination is preferably carried out by the action of powdered zinc. The solvent is preferably acetic acid and the reaction may be carried out at or around room temperature.

In process (U), suitable leaving groups include imidazol-1-yl(thiocabonyl)oxy, which may be introduced by reaction of a corresponding compound in which $R^6$ represents OH with 1,1'-thiocarbonyldiimidazole. Suitable sources of hydride include tributyltin hydride, and the reaction is preferably carried out in the presence of AIBN. Suitable solvents include those which do not adversely affect the reaction, for example benzene. The reaction may be carried out up to the reflux temperature of the solvent.

In process (v), suitable reducing agents include 1,3-propanedithiol. Suitable solvents include those which do not adversely affect the reaction, for example methanol. The reaction is preferably carried out in the presence of triethylamine, and may be carried out at or around room temperature. The azido compound may be produced by the action of azide ion on a corresponding compound in which $R^6$ represents a leaving group, for example triflate.

In process (w), suitable alkylating agents include methyl iodide, and suitable acylating agents include acyl halides, for example acetyl chloride. Suitable solvents include those which do not adversely affect the reaction, for example dichloromethane. The reaction may be carried out at or around room temperature.

In process (x), suitable reducing agents include o L-Selectride. Suitable solvents include those which do not adversely affect the reaction, for example THF. The reaction is preferably carried out below room temperature.

In process (y), suitable oxidizing agents include sodium chlorite, preferably in the presence of 1-methylcyclohex-1-ene. Suitable solvents include those which do not adversely affect the reaction, for example $^t$butanol. The reaction is preferably carried out at or around room temperature.

In process (z), suitable Wittig reagents include (carbomethoxymethylene)triphenylphosphorane. Suitable solvents include those which do not adversely affect the reaction, for example toluene. The reaction may be carried out at or around the reflux temperature of the solvent. Conventional methods may then be used to produce the corresponding acid and amides from the product obtained with this preferred reagent.

Where necessary, hydroxy groups in intermediate compounds may be protected using conventional protecting group chemistry [as described in "Protective Groups in Organic Chemistry", ed: J W F McOmie, Plenum Press (1973), and "Protective Groups in Organic Synthesis", T W Greene, Wiley-Interscience (1981)]. A particularly useful protecting group which may be mentioned is $^t$butyldimethylsilyl.

Compounds in which $R^4$ represents halogen and compounds in which $R^6$ represents a leaving group are useful in the production of corresponding compounds of formula I.

The compounds of formula I may be isolated from their reaction mixtures using conventional techniques.

The compounds of formula I are useful because they possess pharmacological activity in animals; in particular they are useful because they possess immunosuppressive activity, e.g. in the tests set out in Tests A, B, C and D. Thus the compounds are indicated for use in the treatment or prevention of resistance to transplanted organs or tissues, such as kidney, heart, lung, bone marrow, skin, cornea, etc; and of autoimmune, inflammatory, proliferative and hyperproliferative diseases, and of cutaneous manifestations of immunologically-mediated diseases: for example rheumatoid arthritis, lupus erythematosus, systemic lupus erythematosus, Hashimoto's thyroiditis, multiple sclerosis, myasthenia gravis, type 1 diabetes, uveitis, nephrotic syndrome, psoriasis, atopical dermatitis, contact dermatitis and further eczematous dermatitides, seborrheic dermatitis, Lichen planus, Pemphicjus, bullous Pemphigoid, Epidermolysis bullosa, urticaria, angioedemas, vasculitides, erythemas, cutaneous eosinophilias, Alopecia areata, eosinophilic fasciitis, atherosclerosis etc.

The compounds of the invention are also indicated more generally in the treatment of respiratory diseases, for example reversible obstructive airways disease.

Further, the compounds of the invention are indicated in the treatment of a disease selected from intestinal inflammations/allergies such as Coeliac disease, proctitis, eosinophilic gastroenteritis, mastocytosis, Crohn's disease and ulcerative colitis; and food related allergic diseases which have symptomatic manifestation remote from the gasto-intestinal tract, for example migraine, rhinitis and eczema.

The compounds of the invention are also indicated for use as antimicrobial agents, and thus may be used in the treatment of diseases caused by pathogenic microorganisms and the like.

We therefore provide the use of compounds of formula I as pharmaceuticals.

Further, we provide the use of a compound of formula I in the manufacture of a medicament for use as an immunosuppressive agent.

For the above-mentioned therapeutic uses the dosage administered will, of course, vary with the compound employed, the mode of administration, the treatment desired (e.g. topical, parenteral or oral) and the disease indicated. However, in general, satisfactory results are obtained when the compounds are administered at a daily dosage of from 0.001 to 20 mg per kg of animal body weight. For man the indicated total daily dosage is in the range of from 0.01 mg to 1000 mg and preferably from 0.5 mg to 100 mg, which may be administered, for example twice weekly, or in divided doses from 1 to 6 times a day or in sustained release form. Thus unit dosage forms suitable for administration, e.g. oesophageally, comprise from 0.01 mg to 5002 g, and preferably 0.5 mg to 100 mg of the compound preferably admixed with a solid or liquid pharmaceutically acceptable diluent, carrier or adjuvant.

According to our invention we also provide a pharmaceutical composition comprising preferably less than 80%, and more preferably less than 50% by weight, of a compound of formula I in combination with a pharmaceutically acceptable adjuvant, diluent or carrier. Examples Of suitable adjuvants, diluents or carriers are: for tablets, capsules and dragees—microcrystalline cellulose, calcium phosphate, diatomaceous earth, a sugar such as lactose, dextrose or mannitol, talc, stearic acid, starch, sodium bicarbonate and/or gelatin; for suppositories—natural or hardened oils or waxes; and for inhalation compositions—coarse lactose. The compound of formula I preferably is in a form having a mass median diameter of from 0.01 to 10 μm. The compositions may also contain suitable preserving, stabilising and wetting agents, solubilisers (e.g. a water-soluble cellulose polymer such as hydroxypropyl methylcellulose, or a water-soluble glycol such as propylene glycol), sweetening and colouring agents and flavourings. The compositions may, if desired, be formulated in sustained release form.

For the treatment of reversible obstructive airways disease, we prefer the compound of formula I to be administered by inhalation to the lung, especially in the form of a powder.

According to a further aspect of the invention, there is provided a method of effecting immunosuppression which comprises administering a therapeutically effective amount of a compound of formula I, as defined above, to a patient. The compounds of formula I have the advantage that they are less toxic, more efficacious, are longer acting, have a broader range of activity, are more potent, are more stable, produce fewer side effects, are more easily absorbed or have other useful pharmacological properties, than compounds previously used in the therapeutic fields mentioned above.

The compounds of formula I have a number of chiral centres and may exist in a variety of stereoisomers. The invention provides all optical and stereoisomers, as well as racemic mixtures. The isomers may be resolved or separated by conventional techniques.

However, the preferred stereochemistry of various chiral carbon atoms are shown in formula Ia,

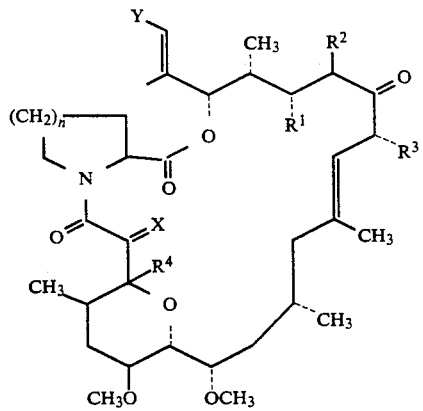

wherein $R^1$ to $R^4$, X and n are as first defined above, and Y represents a cyclic group of formula IIa or IIIA,

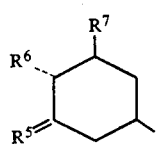

-continued

IIIa in which $R^5$ to $R^8$ are as first defined above.

Test A

Mixed Lymphocyte Reaction (MLR) I

The MLR test was performed in microtitre plates, with each well containing $5 \times 10^5$ C57BL/6 responder cells (H-$2^b$), $5 \times 10^5$ mitomycin C treated (25μg/ml mitomycin C at 37° C. for 30 minutes and washed three times with RPMI 1640 medium) BALB/C stimulator cells (H-$2^d$) in 0.2 ml RPMI 1640 medium supplemented with 10% fetal calf serum, 2 mM sodium hydrogen carbonate, penicillin (50 μg/ml) and streptomycin (50 μg/ml). The cells were incubated at 37° C. in a humidified atmosphere of 5% carbon dioxide and 95% of air for 68 hours and pulsed with $^3$H-thymidine (0.5 μCi) 4 hours before the cells were collected. The object compound of this invention was dissolved in ethanol and further diluted in RPMI 1640 medium and added to the cultures to give final concentrations of 0.1 μg/ml or less.

Test B

Mixed Lymphocyte Reaction (MLR) II

The MLR test was performed in 96-well microtitre plates with each well containing $3 \times 10^5$ cells from each of two responding donors in a final volume of 0.2 ml RPMI 1640 medium supplemented with 10% human serum, L-glutamine and penicillin/streptomycin. The compound under test was dissolved at 10 mg/ml in ethanol and further diluted in RPMI 1640. The cells were incubated at 37° C. in a humidified atmosphere at 5% carbon dioxide for 96 hours. 3H-thymidine (0.5 μCi) was added for the final 24 hours of the incubation to provide a measure of proliferation.

Test C

Graft versus Host Assay (GVH)

Spleen cells from DA and DAxLewis F1 hybrid rats were prepared at approximately $10^8$ cells/ml. 0.1 ml of these suspensions were injected into the rear footpads of DAxLewis F1 rats (left and right respectively). Recipient animals are dosed with the compound under test, either orally or subcutaneously, on days 0–4. The assay is terminated on day 7 when the popliteal lymph nodes of the animals are removed and weighed. The increase in weight of the left node relative to the weight of the right is a measure of the GVH response.

Test D

Inhibition of Interleukin-2 (IL-2) secretion

The test was performed following the method of S Sawada et al, J Immunol (6), Vol 139, pp 1797–1803, but using the Jurkat cell line.

The invention is illustrated, but in no way limited, by the following Examples.

EXAMPLE 1

17-Allyl-14-hydroxy-12-[2-(4-hydroxy-3-methoxycyclohexyl)1-methylvinyl]-1.23,25-trimethoxy-13,19,21,27-tetramethyl-11,28-dioxa-4-azatricyclo[22.3.1.2.0$^{4,9}$]-octacos-18-ene-2.3,10,16-tetraone

(a)

17-Allyl-2,14-dihydroxy-12-[2-(4-hydroxy-3-methoxy cyclohexyl)-1-methylvinyl]-1,23,25-trimethoxy-13,19,21,27-tetramethyl-11,28-dioxa-4-azatricyclo[22.3.1.0$^{4,9}$]octacos-18-ene-3,10,16-trione 17-Allyl-1,2,14-trihydroxy-12-[2-(4-hydroxy-3-methoxy cyclohexyl)-1-methylvinyl]-23,25-dimethoxy-13,19,21,27-tetramethyl-11,28-dioxa-4-azatricyclo[22.3.1.0$^{4,9}$]octacos-18-ene-3,10,16-trione (the compound of Example 5, WO 89/05304) (200 mg) was added to a suspension of montmorillonite K10 (500 mg) in methanol (5 ml). After stirring for 4 days at room temperature a further portion of montmorillonite was added (500 mg) and stirring was continued for a further 2 days. The reaction mixture was then filtered through celite and was concentrated to an oil in vacuo. Column chromatography on silica then gave the subtitle compound as an oil (42 mg).

MS: 843 [M+Na]+; 904 [M+Rb]+

(b)

17-Allyl-14-hydroxy-12-[2-(4-hydroxy-3-methoxycyclohexyl)-1-methylvinyl]-1,23.25-trimethoxy-13,19,21,27-tetramethyl-11,28-dioxa-4-azatricyclo[22.3.1.0$^{4,9}$]octacos-18-ene-2.3,10,16-tetraone The compound of step (a) (40 mg) was dissolved in methanol (3 ml) and to this was added cupric acetate (100 mg). The resulting suspension was stirred and heated to reflux for 30 minutes. The reaction mixture was then cooled, filtered and evaporated in vacuo. Column chromatography on silica gave the title compound (30 mg) as an oil.

MS (FAB): 902.5 [M+Rb]+; 840.8 [M+Na]+; 818.8 [M+H]+; 800.8 [M+H]+; 786.8 [M+H-CH$_3$OH]+

$^{13}$C NMR δ: 211.7 (C16); 197.6 (C2); 169.3 (C10); 166.2 (C3); 139.1 (C29); 130.5 (C31); 123.4 (C18); 116.7 (C42); 102.4 (C1); 102.4 (C1); 50.6 (C1-OCH$_3$)

EXAMPLE 2

17-Allyl-1-amino-14-hydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone and 17-Allyl-1,14-dihydroxy-12-[2-(4-hydroxy-3-methoxycyclohexyl]-1-methylvinyl]-23,25-dimethoxy-2-imino-13,19,21,27-tetramethyl-11,28-dioxa-4-azatricyclo[22.3.1,0$^{4,9}$]octacos-18-ene-3,10,16-trione

(a)

17-Allyl-1-chloro-14-hydroxy-12-[2-(4-hydroxy-3-methoxy cyclohexyl)-1-methylvinyl]-23,25-dimethoxy-13,19,21,27-tetra methyl-11,28-dioxa-4-azatricyclo[22.3.1,0$^{4,9}$]octacos-18-ene-2.3,10,16-tetraone A solution of 17-allyl-1,14-dihydroxy-12-(2-(4-hydroxy-3-methoxycyclohexyl)-1-methylvinyl]-23,25-dimethoxy-13,19,21,27-tetramethyl-ii,28-dioxa-4-azatricyclo (22.3.1.0$^{4,9}$]octacos-18-ene-2,3,10,16-tetraone (FR-900506) (0.6 g) in dry dichloromethane (15 ml) was added dropwise over 5 minutes at room temperature under an atmosphere of nitrogen to a solution of thionyl chloride (544 µl) and pyridine (1.33 ml) in dry dichloromethane (15 ml). After stirring for 5 minutes at room temperature the reaction mixture was added slowly to vigorously stirred saturated aqueous sodium hydrogen carbonate solution (50 ml). After stirring for 5 minutes this mixture was extracted with diethyl ether (150 ml) and the extract washed with dilute aqueous hydrochloric acid (1M, 50 ml), water and brine before being dried (MgSO$_4$), filtered and evaporated in vacuo to give the subtitle compound as a foam (630 mg).

MS: 908.4 [M+Rb]+; 906.4 [M+Rb]+; 870.7 [M-HCl+Rb]+; 844.9 [M+H]+

$^{13}$C NMR (CDCl$_3$) δ: 212.1 (C16); 189.3 (C2); 169.3 (C10); 164.1 (C3); 140.4 (C19); 135.8 (C41); 132.3 (C29); 129.4 (C31); 122.6 (C18); 116.6 (C42); 108.9 (C1); 84.3 (C34); 70.3 (C14); 48.2 (C20); 41.3 (C13); 9.8 (C39)

(b)

17-Allyl-1-amino-14-hydroxy-12-[2-(4-hydroxy-3-methoxy cyclohexyl)-1-methylvinyl]-23,25-dimethoxy-13,19,21,27-tetra methyl-11,28-dioxa-4-azatricyclo[22.3.1.0$^{4,9}$]octacos-18-ene-2.3,10,16-tetraone and 17-Allyl-1,14-dihydroxy-12-[2-(4-hydroxy-3-methoxycyclo hexyl)-1-methylvinyl]-23,25-dimethoxy-2-imino-13,19,21,27-tetramethyl-11,28-dioxa-4-azatricyclo[22,3.1.0$^{4,9}$]octacos-18-ene-3,10,16-trione A crude sample of the compound of step (a) (405 mg) was taken up in THF (tetrahydrofuran) (8 ml) and to this was added concentrated aqueous ammonia solution (4 ml). After stirring for 20 minutes at room temperature the reaction mixture was diluted with water (20 ml) and diethyl ether (50 ml). The organic extract was then separated and washed with brine before being dried (MgSO$_4$), filtered and concentrated in vacuo to a foam. This was chromatographed on silica using HPLC eluting with 2% methanol in diethyl ether to give fraction A (190 mg) and fraction B (98 mg). Fraction A was further purified by chromatography on silica using HPLC eluting with ethyl acetate to give the first title compound (92 mg) as a foam.

MS: 887.5 [M+Rb]+; 803.7 [M+H]+

$^{13}$C NMR (CDCl$_3$) δ: 213 (C16); 198.2 (C2); 169.2 (C10); 166.2 (C3); 139.4 (C19); 135.7 (C41); 132.6 (C29); 129.6 (C31); 122.2 (C18); 116.5 (C42); 88.6 (C1); 84.2 (C34); 76.7 (C12); 75.5 (C23); 71.1 (C24); 70.2 (C14); 56.4 (C9); 52.7 (C17); 48.6 (C20); 43.0 (C15); 39.9 (C13); 38.9 (C5); 31.3 (C36); 30.7 (C37); 27.9 (C8); 26.1 (C21); 24.6 (C6); 21.3 (C7); 20.4 (C44); 14.2 (C30); 9.5 (C39)

Fraction B was further purified by chromatography on silica using HPLC eluting with hexane/acetone [2:1] to give the second title compound (70 mg) as a foam.

MS: 887.5 [M+Rb]+; 825.7 [M+Na]+; 803.7 [M+H]+; 785.7 [M+H-H$_2$O]+; 767.7 [M+H-2H$_2$O]+

$^{13}$C NMR (CDCl$_3$) δ: 214.4 (C16); 175.7 (C2); 169.9 (C10); 168 (C3); 139.1 (C19); 134.7 (C41); 131.3 (C29); 128.2 (C31); 123.4 (C18); 116.7 (C42); 95.5 (C1); 84.2 (C34); 75.2 (C23); 73.4 (C25); 71.5 (C24); 69.5 (C14); 52.9 (C17); 49.8 (C20); 44.9 (C15); 39.6 (C13); 39.3 (C5); 31.2 (C36); 30.8 (C37); 27.7 (C8); 26.2 (C21); 24.3 (C6); 21.0 (C44); 20.0 (C7); 14.5 (C30); 10.2 (C39)

EXAMPLE 3

17-Allyl-1-(1-thiopropyl)-14-hydroxy-12-[2-(4-hydroxy-3-methoxycyclohexyl)-1-methylvinyl]-23,25-dimethoxy-13,19,21,27-tetramethyl-11,28-dioxa-4-azatricyclo [22.3.1.0$^{4,9}$]octacos-18-ene-2.3,10,16-tetraone A solution of the compound of Example 2(a) (100 mg) and propanethiol (0.1 ml) in THF (2 ml) and saturated aqueous sodium hydrogen carbonate solution (2 ml) was stirred vigorously for 24 hours at room temperature. Water (10 ml) was then added and the reaction mixture was extracted with diethyl ether (20 ml). The organic extract was then washed with brine before being dried (MgSO$_4$), filtered and evaporated to an oil in vacuo. Chromatography on silica eluting with hexane/acetone [3:1] then gave the title compound (42 mg) as a foam.

MS: 946 [M+Rb]+; 885 [M+Na]+; 863 [M+H]+; 787 [M+H-CH$_3$(CH$_2$)$_2$SH]+; 769 [M+H-CH$_3$(CH$_2$)$_2$SH-H$_2$O]+

$^{13}$C NMR (CDCl$_3$) δ: 212.8 (C16); 191 (C2); 169.3 (C10); 166.7 (C3); 140.8 (C19); 135.2 (C41); 131.3 (C29); 128.7 (C31); 122.3 (C18); 116.8 (C42); 89.6 (C1); 84.1 (C34); 73.9 (C25); 73.5 (C35); 70.2 (C14); 56.1 (C9); 51.6 (C17); 48.9 (C20); 44.9 (C15); 39.4 (C13); 38.9 (C5); 36.4 (C40); 33.3 (C26); 31.1 (C36); 30.7 (C37); 29.3 (C8); 28.1 (C21); 27.4 (SCH$_2$); 24.4 (C6); 21.8 (SCH$_2$CH$_2$); 21.0 (C44); 14.3 (C30); 13.6 (S(CH$_2$)$_2$ CH$_3$); 10.2 (C39)

EXAMPLE 4

17-Allyl-1-(N-acetyl)amino-14-hydroxy-12-[2-(4-hydroxy-3-methoxycyclohexyl)-1-methylvinyl]-23,25-dimethoxy-13,19,21,27-tetramethyl-11,28-dioxa-4-azatricyclo [22.3.1.0$^{4,9}$]octacos-18-ene-2.3,10,16-tetraone A sample of the first title compound of Example 2 (crude, 100 mg) was taken up in methanol (10 ml) and acetic anhydride (0.6 ml) was added. After being stored at 4° C. for 3 days further acetic anhydride (0.3 ml) was added and the reaction mixture was stored at this temperature for a further 2 days. The reaction mixture was then poured into saturated aqueous sodium hydrogen carbonate solution (100 ml) and this was then extracted with diethyl ether (100 ml). The separated organic extract after washing with brine was dried (MgSO$_4$), filtered and concentrated in vacuo to a foam. Chromatography on silica eluting with dichloromethane/acetone in an increasing acetone gradient then gave material which was further purified by chromatography on silica eluting with ethyl acetate to give the title compound (37 mg) as a foam.

MS: 929.1 [M+Rb]+; 867.9 [M+Na]+; 846 [M+H]+; 769.1 [M+H-H$_2$O-CH$_3$CONH$_2$]+

$^{13}$C NMR (CDCl$_3$) δ: 212 (C16); 190.2 (C2); 169.8 (C10); 169.4 (CH$_3$CONH); 163.1 (C3); 140.2 (C19); 135.6 (C41); 132.2 (C29); 129.4 (C31); 122.2 (C18); 116.4 (C42); 87.8 (C1); 84.2 (C34); 76.8 (C12); 76.3 (C23); 74.9 (C24); 70.4 (C14); 52.7 (C17); 51.2 (C9); 47.8 (C20); 45.1 (C15); 44.1 (C5); 41.6 (C13); 31.3 (C36); 30.6 (C37); 27.3 (C8); 26.0 (C21); 24.3 (C6); 22.9 (CH$_3$CONH); 21.4 (C7); 18.3 (C44); 16.9 (C47); 15.5 (C43); 14.8 (C30); 9.5 (C39)

Further elution then gave the C1 isomeric compound (46 mg).

MS: 929.1 [M+Rb]+; 867.5 [M+Na]+; 845.6 [M+H]+; 827.6 [M+H—OH]+; 768.6 [M+H-H$_2$O-CH$_3$CONH$_2$]+

$^{13}$C NMR (CDCl$_3$) δ: 210.4 (C16); 194.3 (C2); 169.4 (C10); 169.0 (CH$_3$CONH); 166.1 (C3); 137.8 (C19); 135.7 (C41); 131.7 (C29); 129.5 (C31); 123.7 (C18); 116.5 (C42); 89.7 (C1); 84.2 (C34); 77.9 (C12); 76.0 (C24); 74.5 (C23); 69.8 (C14); 39.5 (C13); 28.2 (C21); 27.3 (C8); 25.2 (C6); 23.1 (CH$_3$CONH); 21.5 (C7); 16.9 (C47); 13.2 (C30); 9.9 (C39)

EXAMPLE 5

17-Allyl-1-(N-formyl)amino-14-hydroxy-12-[2-(4-hydroxy-3-methoxycyclohexyl)-1-methylvinyl]-23,25-dimethoxy13,19,21,27-tetramethyl-11,28-dioxa-4-azatricyclo [22.3.1.0$^{4,9}$]octacos-18-ene-2.3,10,16-tetraone a)

17-Allyl-14-$^t$butyldimethylsilyloxy-12-[2-(4-$^t$butyldimethylsilyloxy-3-methoxycyclohexyl)-1-methylvinyl]-23,25-dimethoxy-1-hydroxy-13,19,21,27-tetramethyl-11,28-dioxa-4-azatricyclo[22.3.1.0$^{4,9}$]octacos-18-ene-2.3,10,16-tetraone To a solution of FR-900506 (500 mg, 0.622 mmole) in dry dichloromethane (20 ml) at room temperature under nitrogen was added 2,6-dimethylpyridine (0.4 ml) and $^t$butyldimethylsilyl triflate (362 mg, 1.32 mmole). After 30 minutes at room temperature further $^t$butyldimethylsilyl triflate (362 mg, 1.32 mmole) was added and the reaction mixture was stirred for a further 30 minutes at room temperature. Dichloromethane (30 ml) was then added and the reaction mixture was extracted with dilute aqueous hydrochloric acid (25 ml) and brine (25 ml). The organic extract was dried (MgSO$_4$), filtered and evaporated to an oil in vacuo. Purification by column chromatography on silica eluting with hexane/acetone [9:1] gave the title compound (606 mg, 94%) as an oil.

MS: 1055 [M+Na]+; 1117 [M+Rb]+ b)

17-Allyl-1-chloro-12-[2-(4-$^t$butyldimethylsilyloxy-3-methoxycyclohexyl)-1-methylvinyl]-14-$^t$butyldimethyl silyloxy-23,25-dimethoxy-13,19,21,27-tetramethyl-11,28-dioxa -4-azatricyclo[22.3.1.0$^{4,9}$]octacos-18-ene-2.3,10,16-tetraone A sample of the compound of step (a) (1 g) in dry dichloromethane (10 ml) was added dropwise over 5 minutes to a stirred solution of thionyl chloride (0.35 ml) and pyridine (0.94 ml) in dry dichloromethane (10 ml). After stirring for a further 5 minutes at room temperature the reaction mixture was poured into saturated aqueous sodium hydrogen carbonate solution (50 ml) and this was extracted with diethyl ether (100 ml). The separated organic extract after washing with dilute aqueous hydrochloric acid (1M, 50 ml), water and brine was then dried (MgSO$_4$), filtered and concentrated in vacuo to give the subtitle compound as a foam (1 g).

c) 17-Allyl-1-amino-12-[2-(4-$^t$butyldimethylsilyloxy-3-methoxycyclohexyl)-1-methylvinyl1-14-$^t$butyldimethyl silyloxy-23,25-dimethoxy-l3,19,21,27-tetramethyl-11,28-dioxa -4-azatricyclo[22.3.1.0$^{4,9}$]octacos-18-ene-2.3,10,16-tetraone A sample of the crude subtitle compound from step (b) (744 mg) was dissolved in THF (10 ml) and this was then added dropwise to concentrated aqueous ammonia solution (5 ml). The reaction mixture after being stirred vigorously for 15 minutes was diluted with water (25 ml) and diethyl ether (50 ml). The diethyl ether extract was then separated and was washed with brine before being dried (MgSO$_4$), filtered and concentrated in vacuo to a foam. Chromatography on silica eluting with hexane/ethyl acetate [5:1] then gave the subtitle compound as a foam (250 mg).

d) 17-Allyl-1-(N-formyliamino-12-[2-(4-$^t$butyldimethyl silyloxy-3-methoxycyclohexyl)-1-methylvinyl]-14-$^t$butyldimethylsilyloxy-23,25-dimethoxy-13,19,21,27-tetramethyl-11,28-dioxa-4-azatricyclo[22.3.1.0$^{4,9}$]octacos-18-ene-2.3,10,16-tetraone To a crude sample of the subtitle compound from step (c) (120 mg) in formic acid (4 ml) at room temperature was added acetic anhydride (0.2 ml). After stirring for 4 hours at room temperature the reaction was stored at 4° C. for 16 hours before being poured into saturated aqueous sodium hydrogen carbonate solution (100 ml). After stirring this mixture for 20 minutes at room temperature it was extracted with diethyl ether (50 ml) and this extract was then washed with brine before being dried (MgSO$_4$), filtered and concentrated in vacuo to give the subtitle compound as an oil.

e) 17-Allyl-1-(N-formylamino-14-hydroxy-12-[2-(4-hydroxy-3-methoxycyclohexyl)-1-methylvinyl]-23,25-dimethoxy-13,19,21,27-tetramethyl-11,28-dioxa-4-azatricyclo [22.3.1.0$^{4,9}$]octacos-18-ene-2.3,10,16-tetraone A crude sample of the subtitle compound from step (d) (120 mg) was taken up in methanol (3 ml) and aqueous hydrofluoric acid was added (0.2 ml). After 2 hours at room temperature the reaction mixture was poured into saturated aqueous sodium hydrogen carbonate solution (20 ml) and this was then extracted with diethyl ether (40 ml). The separated organic extract was then washed with brine before being dried (MgSO$_4$), filtered and concentrated in vacuo to a foam. Chromatography on silica eluting with hexane/acetone (2:1) then gave the title compound (30 mg) as a foam.

MS: 915.2 [M+Rb]$^+$; 831.6 [M+H]$^+$; 813.6 [M+H-H$_2$O]$^+$; 768.6 (M+H-H$_2$O-H$_2$NCHO]$^+$ $^{13}$C NMR (CDCl$_3$) δ: 214.6 (C16); 193.6 (C2); 169.2 (C10); 166.1 (C3); 159.9 (NUCOH); 137.2 (C19); 135.3 (C41); 122.6 (C18); 116.5 (C42); 88.7 (Cl); 84 (C34); 77.9 (C12); 69.2 (C14); 56.2 (C9); 48.7 (C20); 43.6 (C15); 39.9 (C13); 24.2 (C6); 20.8 (C44); 16.7 (C47); 14.7 (C43); 14.0 (C30); 11.1 (C39)

EXAMPLE 6

17-Allyl-1-fluoro-14-hydroxy-12-[2-(4-hydroxy-3-methoxycyclo hexyl)-1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone To a cold (0° C.) solution of the subtitle compound of Example 5(a) (250 mg) in dry dichloromethane (10 ml) under nitrogen was added diethylaminosulphur trifluoride (100 mg). After stirring for 2 hours at 0° C. the reaction mixture was poured into saturated aqueous sodium hydrogen carbonate solution (30 ml) and this was then extracted with diethyl ether (100 ml). The separated organic extract after washing with brine was dried (MgSO$_4$), filtered and concentrated in vacuo to a foam (248 mg). This was then dissolved in acetonitrile (10 ml) and 40% aqueous hydrofluoric acid (0.2 ml) was added. After being stirred for two hours at room temperature the reaction mixture was poured into saturated aqueous sodium hydrogen carbonate solution (50 ml) and this was then extracted with diethyl ether (100 ml). The separated organic extract was then washed with brine and was dried (MgSO$_4$), filtered and concentrated in vacuo to an oil. Chromatography on silica eluting with dichloromethane/acetonitrile [2:1 ] then gave the title compound (28 mg) as a foam.

MS: 890.5 [M+Rb]$^+$; 828.9 [M+Na]$^+$; 787 [M+H-HF]$^+$; 769 [M+H-HF-H$_2$O]$^+$ $^{19}$F NMR δ: −139.55 (d,J=28.15Hz); −141.55 (d,J=28.15Hz) (two rotamers)

$^{13}$C NMR (CDCl$_3$) δ: 211.9 (C16); 192.3 (C2); 169 (C10); 164.2 (C3); 140 (C19); 135.6 (C41); 132 (C29); 129.5 (C31); 122.8 (C18); 116.5 (C42); 112.8 (Cl); 84.2 (C34); 77.2 (C12); 76.0 (C23); 75.1 (C25); 73.5 (C35); 72.5 (C24); 69.8 (C14); 48.1 (C20); 45 (C5); 43.8 (C15); 40.8 (C13); 32.3 (C26); 31.2 (C36); 30.7 (C37); 26.8 (C8); 25.9 (C21); 25.0 (C6); 21.7 (C7); 19.4 (C44); 15.8 (C47); 15.1 (C43); 14.5 (C30) ; 9.7 (C39)

EXAMPLE 7

The first title compound of Example 2 was tested in Test D, and found to inhibit IL-2 secretion by 50% (IC$_{50}$) at a o concentration of $2 \times 10^{-10}$M.

EXAMPLE 8

17-Allyl-1,14-dihydroxy-12-[2-(cyclopentyl-3-carboxaldehyde) -1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone (a) 17-Allyl-1-hydroxy-12-[2-(4-hydroxy-3-methoxycyclo hexyl)-1-methylvinyl]-14-$^t$butyldimethylsilyloxy-23,25-dimethoxy-13,19,21,27-tetramethyl-11,28-dioxa-4-azatricyclo [22.3.1.0$^{4,9}$]octacos-18-ene-2.3,10,16-tetraone A solution of the product from Example 5(a) (1.28 g) in methanol (100 ml) containing pyridinium p-toluene sulphonate was stirred for 18 hours at room temperature. Volatiles were then removed in vacuo and the residue was dissolved in diethyl ether. The ethereal solution after washing with saturated aqueous sodium hydrogen carbonate solution, dilute aqueous hydrochloric acid (1N), saturated aqueous sodium hydrogen carbonate solution and brine was dried (MgSO$_4$), filtered and evaporated in vacuo to give the subtitle compound as a pale yellow foam (0.97 g).

(b) 17-Allyl-1-hydroxy-12-[2-(4-trifluoromethylsulphonyloxy -3-methoxycyclohexyl)-1-methylvinyl]-14-$^t$butyl-dimethyl silyloxy-23,25-dimethoxy-13,19,21,27-tetramethyl-11,28-dioxa -4-azatricyclo[22.3.1.0$^{4,9}$]octacos-18-ene-2.3,10,16-tetraone To a cold (−10° C.) stirred solution of the product of step (a) (0.97 g) in dry dichloromethane (25 ml) under nitrogen was added trifluoromethanesulphonic anhydride (0.1 ml). After stirring for 15 minutes at −10° C., saturated aqueous sodium hydrogen carbonate solution was added and the reaction mixture was extracted with diethyl ether. The ether extracts were then washed with saturated aqueous sodium hydrogen carbonate solution, dilute aqueous hydrochloric acid (1N), saturated aqueous sodium hydrogen carbonate solution and brine before being dried (MgSO$_4$), filtered and concentrated in vacuo to give the title compound as an oil (0.95 g).

(c)
17-Allyl-1-hydroxy-12-[2-(cyclopentyl-3-carboxaldehyde)
-1-methylvinyl]-14-$^t$butyldimethylsilyloxy-23,25-dimethoxy-13,19,21,27-tetramethyl-11,28-dioxa-4-azatricyclo [22.3.1.0$^{4,9}$]octacos-18-ene-2.3,10,16-tetraone Silica (55 g, Merck Kieselgel 60) was added to a solution of the product from step (b) (0.9 g) in dichloromethane (250 ml). Volatiles were then removed in vacuo at room temperature and the resulting freely flowing powder was stored at 8° C. for 16 hours. The support was then washed with ethyl acetate and 10% acetone in ethyl acetate containing 2,6-dimethylpyridine. The combined organic extracts after washing with saturated aqueous sodium hydrogen carbonate solution, dilute aqueous hydrochloric acid (1N), saturated aqueous sodium hydrogen carbonate solution and brine were dried (MgSO$_4$), filtered and concentrated to an oil in vacuo. Chromatography on silica eluting with hexane in an acetone gradient then gave the title compound (0.126 g) as a foam.

(d)
17-Allyl-1,14-dihydroxy-12-[2-(cyclopentyl-3-carboxaldehyde)-1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone To a solution of the compound of step (c) (25 mg) in acetonitrile (5 ml) was added 40% aqueous hydrofluoric acid (1 ml). After stirring for 1 hour at room temperature the reaction mixture was poured into saturated aqueous sodium hydrogen carbonate solution and the mixture was extracted with diethyl ether. The organic extract was then dried, (MgSO$_4$), filtered and evaporated to an oil in vacuo. Chromatography on silica eluting with acetone/hexane [1:2] then gave the title compound (18 mg) as a foam.

EXAMPLE 9

1,14-dihydroxy-12-[2-(cyclopentyl-3-carboxaldehyde)-1-methylvinyl]-23,25-dimethoxy-17-propyl-13,19,21,27-tetramethyl-11,28-dioxa-4-azatricyclo[22.3.1.0$^{4,9}$]octacos-18-ene-2.3,10,16-tetraone To a solution of the product of Example 8 (15 mg) in methanol (4 ml) was added Pd-on-C (4 mg, 10%) and the resulting suspension was then stirred in an atmosphere of hydrogen for 1 hour at 0° C. The reaction mixture was then filtered and volatiles were removed in vacuo. Chromatography on silica then gave the title compound as a foam (13 mg).

EXAMPLE 10

17-Allyl-1,14-dihydroxy-12-[2-(cyclopentyl-3-methanol)-1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone (a)
17-Allyl-1-hydroxy-12-[2-(cyclopentyl-3-methanol)-1-methylvinyl]-14-$^t$butyldimethylsilyloxy-23,25-dimethoxy-13,19,21,27-tetramethyl-11,28-dioxa-4-azatricyclo [22.3.1.0$^{4,9}$]octacos-18-ene-2.3,10,16-tetraone To a solution of the product of Example 8(c) (170 mg) in dry THF (15 ml) at −70° C. was added a solution of L-selectride in THF (1M) slowly under nitrogen until no starting material remained (0.4 ml). Saturated aqueous ammonium chloride solution (0.5 ml) was then added at −70° C. followed by aqueous hydrogen peroxide solution (30% by weight, 1 ml) and ethanolamine (0.1 ml). After warming to 0° C. the reaction mixture was extracted with diethyl ether and this was washed with water (x2), dilute aqueous hydrochloric acid (1N) and saturated aqueous sodium hydrogen carbonate solution, before being dried (MgSO$_4$), filtered and evaporated to an oil in vacuo. Chromatography on silica eluting with acetone/hexane [2:7] then gave the title compound (151 mg) as a foam.

MS (FAB): 911 [M+Na]$^+$; 972 [M+Rb]$^+$.

(b)
17-Allyl-1,14-dihydroxy-12-[2-(cyclopentyl-3-methanol)-1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone To a solution of the product of step (a) (150 mg) in acetonitrile (20 ml) was added 40% aqueous hydrofluoric acid (3 ml). After stirring for 1 hour at room temperature the reaction mixture was poured into saturated aqueous sodium hydrogen carbonate solution and the mixture was extracted with diethyl ether. The organic extracts were then dried, (MgSO$_4$), filtered and evaporated to an oil in vacuo. Chromatography on silica eluting with acetone/hexane [1:3] then gave the title compound (130 mg) as a foam.

MS (plasma spray): 738.54 [M+H-2H$_2$O]$^+$; 756.58 (M+H-H$_2$O]$^+$; 774.6 [M+H]$^+$; 791.57 [M+NH$_4$]$^+$ $^{13}$C NMR (CDCl$_3$) δ: (Major rotamer) 212.5 (C16); 196.2 (C2); 169 (C10); 164.7 (C3); 138.8 (C19); 135.5 (C40); 131.4 (C31); 131 (C29); 122.4 (C18); 116.5 (C41); 97 (C1); 77.7 (C12); 75 (C23); 69.9 (C14); 67 (C37); 56.5 (C9); 48.5 (C20); 43.6 (C15); 27.6 (C8); 26 (C21); 24.4 (C6); 20.9 (C7); 20.3 (C43); 13.9 (C30); 9.5 (C38)

EXAMPLE 11

1,14-dihydroxy-12-[2-(cyclopentyl-3-methanol)-1-methylvinyl]-23,25-dimethoxy-17-propyl-13,19,21,27-tetramethyl-11,28-dioxa-4-azatricyclo[22.3.1.0$^{4,9}$]octacos-18-ene-2.3,10,16-tetraone To a solution of the title compound of Example 10 (22 mg) in methanol (10 ml) was added 10% Pd-on-C (5 mg) and the resulting suspension was then stirred in an atmosphere of hydrogen for 2 hours at 0° C. The reaction mixture was then filtered and volatiles were removed in vacuo. Chromatography on silica then gave the title compound as a foam (18 mg).

MS (plasma spray): 794 [M+NH$_4$]$^+$

EXAMPLE 12

17-Allyl-1-hydroxy-12-[2-(cyclopentyl-3-carboxylic acid)
-1-methylvinyl]-14-$^t$butyldimethylsilyloxy-23,25-dimethoxy-13,19,21,27-tetramethyl-11,28-dioxa-4-azatricyclo [22.3.1.0$^{4,9}$]octacos-18-ene-2,3,10,16-tetraone To a solution of the product of Example 8(c) (393 mg) in $^t$butanol (30 ml) containing 1-methylcyclohex-1-ene (4 ml) was added dropwise a solution of sodium chlorite (0.75 g) and sodium phosphate (0.75 g) in distilled water (10 ml). After stirring for 10 minutes at room temperature the reaction mixture was partitioned between ethyl acetate and water and the organic extract was separated. This was then washed with aqueous sodium phosphate solution, an aqueous sodium thiosulphate/sodium phosphate mixture and aqueous sodium phosphate solution before being dried (MgSO$_4$), filtered and evaporated in vacuo to give the title compound (350 mg) as a foam.

EXAMPLE 13

17-Allyl-1,14-dihydroxy-12-[2-(cyclopentyl-3-carboxylic acid)-1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone To a solution of the product of Example 12 (350 mg) in acetonitrile (30 ml) was added 40% aqueous hydrofluoric acid (3 ml). After stirring for 1.5 hours at room temperature the reaction mixture was poured into ethyl acetate and the organic extract was washed with water and saturated aqueous sodium phosphate solution (x4) before being dried (MgSO$_4$), filtered and evaporated to an oil in vacuo. Chromatography on silica eluting with acetone/hexane/acetic acid [40:10:1] then gave the title compound (32 mg) as a foam.

MS (FAB): 771.02 [M—OH+H]$^+$; 811 [M+Na]$^+$; 872.72 [M+Rb]$^+$ $^{13}$C NMR δ: (major rotamer) 212.6 (C16); 196.1 (C2); 181.6 (C37); 169.1 (C10); 164.7 (C3); 138.9 (C19); 135.6 (C40); 132.7 (C29); 130.3 (C31); 122.6 (C18); 116.7 (C41); 98.6 (Cl); 77.8 (C12); 75.3 (C23); 73.6 (C25); 72.6 (C24); 70.0 (C14); 56.7 (C9); 52.9 (C17); 48.7 (C20); 26.3 (C21); 24.6 (C6); 21.1 (C7); 20.4 (C43); 14.1 (C30); 9.7 (C38).

EXAMPLE 14

17-Allyl-1,14-dihydroxy-12-[2-cyclopentyl-3-carboxylic acid methyl ester)-1-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone To a solution of the product of Example 13 (25 mg) in diethyl ether (5 ml) at 0° C. was added diazomethane. Volatiles were then removed in vacuo to give the title compound as a foam (25 mg).

EXAMPLE 15

1,14-dihydroxy-12-[2-(cyclopentyl-3-carboxylic acid methyl ester)-1-methylvinyl]-23,25-dimethoxy-17-propyl-13,19,21,27-tetramethyl-11,28-dioxa-4-azatricyclo[22.3.1.0$^{4,9}$]octacos-18-ene-2.3,10,16-tetraone To a solution of the product of Example 14 (20 mg) in methanol (10 ml) was added 10% Pd-on-C (4 mg) and the resulting suspension was then stirred in an atmosphere of hydrogen for 2 hours at 0° C. The reaction mixture was then filtered and volatiles were removed in vacuo. Chromatography on silica then gave the title compound as a foam (17 mg).

EXAMPLE 16

1,14-dihydroxy-12-[2-(cyclopentyl-3-carboxylic acid) -1-methylvinyl]-23,25-dimethoxy-17-propyl-13,19,21,27-tetramethyl-11,28-dioxa-4-azatricyclo[22.3.1.0$^{4,9}$]octacos-18-ene-2.3,10,16-tetraone To a solution of the product of Example 15 (18 mg) in methanol (10 ml) was added 10% Pd-on-C (4 mg) and the resulting suspension was then stirred in an atmosphere of hydrogen for 2 hours at 0° C. The reaction mixture was then filtered and volatiles were removed in vacuo. Chromatography on silica then gave the title compound as a foam (17 mg).

MS (FAB): 874 [M+Rb]$^+$

EXAMPLE 17

17-Allyl-1-hydroxy-12-[2-(cyclopentyl-3-methyl propenoate)-1-methylvinyl[-14-$^t$butyldimethylsilyloxy-23,25-dimethoxy-13,19,21,27-tetramethyl-11,28-dioxa-4-azatricyclo[22.3.1.0$^{4,9}$]octacos-18-ene-2.3,10,16-tetraone A solution of the product of Example 8(d) (140 mg) and (carbomethoxymethylene)triphenylphosphorane (140 mg) in dry distilled toluene (10 ml) was stirred and heated at 70° C. for one hour. After stirring at room temperature overnight the reaction mixture was diluted with diethyl ether and this was then washed with saturated aqueous sodium hydrogen carbonate solution and brine. The organic extract was then dried (MgSO$_4$), filtered and evaporated to an oil in vacuo. Chromatography on silica eluting with hexane in an increasing diethyl ether gradient then gave the title compound (70 mg) as a foam.

EXAMPLE 18

17-Allyl-1,14-dihydroxy-12-[2-(cyclopentyl-3-methyl propenoate)-1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone To a solution of the product of Example 17 (70 mg) in acetonitrile (10 ml) was added 40% aqueous hydrofluoric acid (1 ml). After stirring for 1 hour at room temperature the reaction mixture was poured into saturated aqueous sodium hydrogen carbonate solution and the mixture was extracted with diethyl ether. The combined ether extracts, after washing with saturated aqueous sodium hydrogen carbonate solution, were dried (MgSO$_4$), filtered and concentrated to an oil in vacuo. Chromatography on silica eluting with hexane in an increasing acetone gradient then gave the title compound (55 mg) as a foam.

MS (plasma spray): 792.78 [M+H-2H$_2$O]$^+$; 810.80 [M+H-H$_2$O]$^+$; 828.86 [M+H]$^+$; 845.84 [M+NH$_4$]$^+$ MS (negative plasma spray): 826.09 [M-H]$^+$ $^1$H NMR (CDCl$_3$) δ: 6.93 (1H, dd, J=8.1 and 16.6 Hz); 5.78 (1H, d, J=5.78 Hz), 3.71 (3H, s, CO$_2$Me)

$^{13}$C NMR δ: (Major rotamer) 212.4 (C16); 196.1 (C2); 153.3 (C38); 138.8 (C19); 135.4 (C43); 122.6 (C18); 119 (C37); 116.6 (C44); 97.1 (C1); 56.6 (C9); 51.3 (C40); 9.7 (C41).

EXAMPLE 19

1,14-dihydroxy-12-[2-(cyclopentyl-3-carboxaldehyde)-1-methyl vinyl]-23,25-dimethoxy-17-ethyl-13,19,21,27-tetramethyl-11,28-dioxa-4-azatricyclo[22.3.1.0$^{4,9}$]octacos-18-ene-2.3,10,16-tetraone (a)

1-hydroxy-12-[2-(cyclopentyl-3-carboxaldehyde)-1-methyl vinyl[-14-$^t$butyldimethylsilyloxy-23,25-dimethoxy-17-ethyl-13,19,21,27-tetramethyl-11,28-dioxa-4-azatricyclo [22.3.1,0$^{4,9}$]octacos-18-ene-2.3,10,16-tetraone The subtitle compound was prepared from FR-900520 in a manner analogous to the compound of Example 8(c).

(b)
1,14-dihydroxy-12-[2-(cyclopentyl-3-carboxaldehyde)-1-methylvinyl]-23,25-dimethoxy-17-ethyl-13,19,21,27-tetramethyl-11,28-dioxa-4-azatricyclo[22.3.1.0$^{4,9}$]octacos-18-ene-2.3,10,16-tetraone The product of step (a) was deprotected following the method of Example 8(d) to give the title compound.

EXAMPLE 20

1,14-dihydroxy-12-[2-(cyclopentyl-3-methanol)-1-methylvinyl]-23,25-dimethoxy-17-ethyl-13,19,21,27-tetramethyl-11,28-dioxa-4-azatricyclo[22.3.1,0$^{4,9}$]octacos-18-ene-2.3,10,16-tetraone The product of Example 19 was reduced by the method of Example 10(a) to give the title compound.
MS (plasma spray): 779 [M+NH$_4$]+

EXAMPLE 21

1,14-dihydroxy-12-[2-(cyclopentyl-3-carboxylic acid)-1-methylvinyl]-23,25-dimethoxy-17-ethyl-13,19,21,27-tetramethyl-11,28-dioxa-4-azatricyclo[22.3.1.0$^{4,9}$]octacos-18-ene-2.3,10,16-tetraone Oxidation of the product of Example 19(a) following the method of Example 12 and then deprotection following the method of Example 13 gave the title compound.
MS (FAB) : 709 [M+Na]+

EXAMPLE 22

1,14-dihydroxy-12-[2-(cyclopentyl-3-carboxylic acid methyl ester)-1-methylvinyl]-23,25-dimethoxy-17-ethyl-13,19,21,27-tetramethyl-11,28-dioxa-4-azatricyclo[22.3.1.0$^{4,9}$]octacos-18-ene-2.3,10,16-tetraone Esterification of the product of Example 21 following the method of Example 14 yielded the title compound.

EXAMPLE 23

1,14-dihydroxy-12-[2-(cyclopentyl-3-methyl propenoate)-1-methylvinyl]-23,25-dimethoxy-17-ethyl-13,19,21,27-tetramethyl-11,28-dioxa-4-azatricyclo[22.3.1.0$^{4.9}$]octacos-18-ene-2.3,10,16-tetraone Wittig reaction on the product of Example 19(a) following the method of Example 17 and then deprotection following the method of Example 18 gave the title compound.
MS (plasma spray): 834 [M+NH$_4$]+

EXAMPLE 24

1-Hydroxy-12-[2-(cyclopentyl-3-carboxaldehyde)-1-methylvinyl]-23,25-dimethoxy-17-propyl-13,19,21,27-tetramethyl-11,28-dioxa-4-azatricyclo[22.3.1.0$^{4,9}$]octacos-18-ene-2,3,10,16-tetraone a)
1-Hydroxy-12-[2-(4-trifluoromethylsulphonyloxy-3-methoxycyclohexyl)-1-methylvinyl]-23,25-dimethoxy-17-propyl-13,19,21,27-tetramethyl-11,28-dioxa-4-azatricyclo [22.3.1.0$^{4,9}$]octacos-18-ene-2.3,10,16-tetraone To a cold (−10° C.), stirred solution of 1-hydroxy-12-[2-(4-hydroxy-3-methoxycyclohexyl)-1-methylvinyl]-23,25-dimethoxy-17-propyl-13,19,21,27-tetramethyl-11,28-dioxa-4-azatricyclo (22.3.1.0$^{4,9}$]octacos-18-ene-2,3,10,16-tetraone (Example 12, WO 89/05304) (0.3 g) in dry dichloromethane (12 ml) under nitrogen was added trifluoromethanesulphonic anhydride (0.1 ml) until no starting material remained. Saturated aqueous sodium hydrogen carbonate solution was then added and the reaction mixture was extracted with diethyl ether. The ether extracts, after washing with saturated aqueous sodium hydrogen carbonate solution, dilute aqueous hydrochloric acid (1N), and saturated aqueous sodium hydrogen carbonate solution, were dried (MgSO$_4$), filtered and concentrated in vacuo to give the title compound as an oil (300 mg).

b)
1-Hydroxy-12-[2-(cyclopentyl-3-carboxaldehyde-1-methylvinyl]-23,25-dimethoxy-17-propyl-13.19.21.27-tetramethyl-11,28-dioxa-4-azatricyclo[22.3.1.0$^{4,9}$]octacos-18-ene-2.3,10,16-tetraone Silica (18 g, Merck Kieselgel 60) was added to a solution of the product of step (a) (300 mg) in dichloromethane (100 ml). Volatiles were then removed in vacuo at room temperature and the resulting freely flowing powder was stored at 8° C. for 16 hours. The support was then washed with acetone containing triethylamine and the solvent was evaporated in vacuo to an oil. Chromatography on silica eluting with hexane in an acetone gradient then gave the title compound as a foam (51 mg).

EXAMPLE 25

1-Hydroxy-12-[2-(cyclopentyl-3-methanol)-1-methylvinyl]-23,25-dimethoxy-17-propyl-13.19.21.27-tetramethyl-11,28-dioxa-4-azatricyclo[22.3.1.0$^{4,9}$]octacos-18-ene-2.3,10,16-tetraone Reduction of the product of Example 24 following the method of Example 10(a) yielded the title compound.

EXAMPLE 26

1-hydroxy-12-[2-(cyclopentyl-3-carboxylic acid)-1-methyl vinyl]-23,25-dimethoxy-17-propyl-13,19,21,27-tetramethyl-11,28-dioxa-4-azatricyclo[22.3.1,0$^{4,9}$]octacos-18-ene-2.3,10,16-tetraone Oxidation of the product of Example 24 using the method of Example 12 gave the title compound.

EXAMPLE 27

1-Hydroxy-12-[2-(cyclopentyl-3-carboxylic acid methylester)-1-methylvinyl]-23,25-dimethoxy-17-propyl-13.19,21.27-tetramethyl-11,28-dioxa-4-azatricyclo[22.3.1.0$^{4,9}$]octacos-18-ene-2.3,10,16-tetraone Esterification of the product of Example 18 using diazomethane following the method of Example 14 gave the title compound.

EXAMPLE 28

1-Hydroxy-12-[2-(cyclopentyl-3-methyl propenoate)-1-methyl vinyl]-23,25-dimethoxy-17-propyl-13,19,21,27-tetramethyl-11,28-dioxa-4-azatricyclo[22.3.1.0$^{4,9}$]octacos-18-ene-2.3,10,16-tetraone Wittig reaction with the product of Example 24 following the method of Example 17 yielded the title compound.

EXAMPLE 29

1-Hydroxy-12-[2-(cyclopentyl-3-carboxaldehyde)-1-methyl vinyl]-23,25-dimethoxy-17-ethyl-13,19,21,27-tetramethyl-11,28-dioxa-4-azatricyclo[22.3.1.0$^{4,9}$]octacos-18-ene-2.3,10,16-tetraone (a)

1-hydroxy-12-[2-(4-hydroxy-3-methoxycyclohexyl)-1-methylvinyl]-23,25-dimethoxy-17-ethyl-13.19,21,27-tetra methyl-11,28-dioxa-4-azatricyclo[22.3.1.0$^{4,9}$]octacos-14,18-ene-2.3,10,16-tetraone 1,14-dihydroxy-12-[2-(4-hydroxy-3-methoxycyclohexyl)-1-methylvinyl)-23,25-dimethoxy-13,19,21,27-tetramethyl-11,28-dioxa-4-azatricyclo[22.3.1.0$^{4,9}$]octacos-18-ene-2,3,10,16-tetraone (FR-900520) (100 mg) and p-toluenesulphonic acid (2 mg) were dissolved in dry toluene (20 ml) and were heated for 2 hours at 100° C. under an atmosphere of nitrogen. Removal of solvent in vacuo and chromatography on silica eluting with hexane/acetone [2:1] gave the sub-title compound as a foam (80 mg).

MS (FAB): 774.8 [M+H]$^+$; 796.85 [M+Na]$^+$; 858.71 [M+Rb]$^+$.

$^{13}$C NMR δ: (major rotamer) 201.15 (C16); 196.0 (C2); 169.2 (C10); 165.1 (C3); 147.8 (C15); 138.0 (C19); 123.82 (C18); 97.88 (C1); 84.05 (C34).

(b)

1-Hydroxy-12-[2-(4-hydroxy-3-methoxycyclohexyl)-1-methylvinyl]-23,25-dimethoxy-17-ethyl-13,19,21,27-tetra methyl-11,28-dioxa-4-azatricyclo[22.3.1.0$^{4,9}$]octacos-18-ene-2.3,10,16-tetraone A sample of the product from step (a) was dissolved in methanol (20 ml) and 10% Pd-on-carbon (10 mg) was added. The mixture was stirred in an atmosphere of hydrogen for 1.5 hours at room temperature and pressure, and was then filtered through celite and evaporated to an oil in vacuo. Column chromatography on silica eluting with hexane/acetone [2:1] gave the subtitle compound as a foam (50 mg).

MS (FAB): 776 [M+H]$^+$; 798 [M+Na]$^+$; 860 [M+Rb]$^+$.

$^{13}$C NMR δ: (major rotamer) 212.34 (C16); 196.42 (C2); 169.38 (C10); 165.16 (C3); 138.9 (C19); 124.16 (C18); 97.41 (C1) ; 84.19 (C34).

c)

1-Hydroxy-12-[2-(cyclopentyl-3-carboxaldehyde)-1-methylvinyl]-23,25-dimethoxy-17-ethyl-13,19,21,27-tetramethyl-11,28-dioxa-4-azatricyclo[22.3.1.0$^{4,9}$]octacos-18-ene-2.3,10,16-tetraone The title compound was Prepared from the product of step (b) using the method of Example 1.

EXAMPLE 30

1-Hydroxy-12-f2-(cyclopentyl-3-methanol)-1-methylvinyl]-23,25-dimethoxy-17-ethyl-13,19,21,27-tetramethyl-11,28-dioxa-4-azatricyclo[22.3.1.0$^{4,9}$]octacos-18-ene-2.3,10,16-tetraone Reduction of the product of Example 29 using the method of Example 10(a) yielded the title compound.

EXAMPLE 31

1-Hydroxy-12-[2-(cyclopentyl-3-carboxylic acid)-1-methyl vinyl]-23,25-dimethoxy-17-ethyl-13,19,21,27-tetramethyl-11.28-dioxa-4-azatricyclo[22.3.1.0$^{4,9}$]octacos-18-ene-2.3,10,16-tetraone Oxidation of the product from Example 29 following the method of Example 12 gave the title compound.

EXAMPLE 32

1-Hydroxy-12-[2-(cyclopentyl-3-carboxylic acid methyl ester)-1-methylvinyl]-23.25-dimethoxy-17-ethyl-13.19.21.27-tetramethyl-11,28-dioxa-4-azatricyclo[22.3.1.0$^{4,9}$]octacos-18-ene-2.3,10,16-tetraone Esterification of the product of Example 31 using the method of Example 14 yielded the title compound.

EXAMPLE 33

1-Hydroxy-12-f2-(cyclopentyl-3-methyl propenoate)-i-methylvinyl]-23,25-dimethoxy-17-ethyl-13,19,21,27-tetramethyl-11,28-dioxa-4-azatricyclo[22.3.1,0$^{4,9}$]octacos-18-ene-2.3,10,16-tetraone Wittig reaction of the product of Example 29 following the method of Example 17 gave the title compound.

EXAMPLE 34

17-Allyl-1-hydroxy-12-[2-(cyclopentyl-3-carboxaldehyde)-1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone The title compound was prepared from 17-allyl-1-hydroxy-12-(2-(4-hydroxy-3-methoxycyclohexyl)-1-methylvinyl]-23,25-dimethoxy-13,19,21,27-tetramethyl-11,28-dioxa-4-azatricyclo (22.3.1.0$^{4,9}$)octacos-18-ene-2,3,10,16-tetraone (Example 17, WO 89/05304) using the method of Example 8(c).

EXAMPLE 35

17-Allyl-1-hydroxy-12-f2-(cyclopentyl-3-methanol)-1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone Reduction of the product from Example 34 following the method of Example 10(a) gave the title compound.

EXAMPLE 36

17-Allyl-1-hydroxy-12-[2-(cyclopentyl-3-carboxylic acid)-1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone Oxidation of the product of Example 34 following the method of Example 12 yielded the title compound.

EXAMPLE 37

17-Allyl-1-hydroxy-12-[2-(cyclopentyl-3-carboxylic acid methyl ester)-1-methylvinyl]-23.25-dimethoxy-13,19,21,27-tetramethyl-11,28-dioxa-4-azatricyclo[22.3.1.0$^{4,9}$]octacos18-ene-2.3,10,16-tetraone Esterification of the product of Example 36 using the method of Example 14 gave the title compound.

EXAMPLE 38

17-Allyl-1-hydroxy-12-[2-(cyclopentyl-3-methyl propenoate)
-1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone Wittig reaction of the product of Example 34 following the method of Example 17 yielded the title compound.

EXAMPLE 39

17-Allyl-1,14-dihydroxy-12-[2-(4(S)-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone (a)

17-Allyl-1-hydroxy-12-[2-(4-$^t$butyldimethylsilyloxy-3-methoxycyclohexyl)-1-methylvinyl]-14-$^t$butyldimethylsilyl
oxy-23,25-dimethoxy-13,19,21,27-tetramethyl-11,28-dioxa-4-azatricyclo[22.3.1.0$^{4,9}$]octacos-18-ene-2.3,10,16-tetraone The subtitle compound was prepared as in Example 5(a) (1.28 g).

(b)

17-Allyl-1-hydroxy-12-[2-(4-hydroxy-3-methoxycyclohexyl)-1-methylvinyl]-14-$^t$butyldimethyl silyloxy-23,25-dimethoxy-13,19,21,27-tetramethyl-11,28-dioxa-4-azatricyclo[22.3,1.0$^{4,9}$]octacos-18-ene-2.3,10,16-tetraone A solution of the product from step (a) in methanol (100 ml) containing pyridinium p-toluene sulphonate was stirred for 18 hours at room temperature. Volatiles were then removed in vacuo and the residue was dissolved in diethyl ether. The ethereal solution after washing with saturated aqueous sodium hydrogen carbonate solution, dilute aqueous hydrochloric acid (1N), saturated aqueous sodium hydrogen carbonate solution and brine was dried (MgSO$_4$), filtered and evaporated in vacuo to give the subtitle compound as a pale yellow foam (0.97 g).

(c)

17-Allyl-1-hydroxy-12-[2-(4-trifluoromethylsulphonyloxy -3-methoxycyclohexyl)-1-methylvinyl]-14-$^t$butyldimethyl silyloxy-23,25-dimethoxy-13,19,21,27-tetramethyl-11,28-dioxa
-4-azatricyclo[22.3.1.0$^{4,9}$]octacos-18-ene-2.3,10,16-tetraone To a cold (−10° C.) stirred solution of the product of step (b) (0.97 g) in dry dichloromethane (25 ml) under nitrogen was added trifluoromethanesulphonic anhydride (0.1 ml). After stirring for 15 minutes at −10° C. saturated aqueous sodium hydrogen carbonate solution was added and the reaction mixture was extracted with diethyl ether. The ether extracts were then washed with saturated aqueous sodium hydrogen carbonate solution, dilute aqueous hydrochloric acid (1N), saturated aqueous sodium hydrogen carbonate solution and brine before being dried (MgSO$_4$), filtered and concentrated in vacuo to give the title compound as an oil (0.95 g).

(d)

17-Allyl-1-hydroxy-12-[2-(4(S)-hydroxy-3-methoxycyclo hexyl)-1-methylvinyl]-14-$^t$butyldimethylsilyloxy-23,25-dimethoxy-13,19,21,27-tetramethyl-11,28-dioxa-4-azatricyclo [22.3.1.0$^{4,9}$]octacos-18-ene-2.3,10,16-tetraone Silica (55 g, Merck Kieselgel 60) was added to a solution of the product of step (a) (0.9 g) in dichloromethane (250 ml). Volatiles were then removed in vacuo at room temperature and the resulting freely flowing powder was stored at 8° C. for 16 hours. The support was then washed with ethyl acetate and 10% acetone in ethyl acetate containing 2,6-dimethyl pyridine. The combined organic extracts after washing with saturated aqueous sodium hydrogen carbonate solution, dilute aqueous hydrochloric acid (1N), saturated aqueous sodium hydrogen carbonate solution and brine were dried (MgSO$_4$), filtered and concentrated to an oil in vacuo. Chromatography on silica eluting with hexane in an acetone gradient then gave the title compound (0.28 g) as a foam.

(e)

17-Allyl-1,14-dihydroxy-12-f2-(4(S)-hydroxy-3-methoxy cyclohexyl)-1-methylvinyl]-23,25-dimethoxy-13,19,21,27-tetra methyl-11,28-dioxa-4-azatricyclo[22.3.1.0$^{4,9}$]octacos-18-ene-2,3,10,16-tetraone To a solution of the product of step (d) (0.28 g) in acetonitrile (10 ml) was added 40% aqueous hydrofluoric acid (2 ml). After stirring for 1 hour at room temperature the reaction mixture was poured into saturated aqueous sodium hydrogen carbonate solution and the mixture was extracted with diethyl ether. The organic extract was then dried (MgSO$_4$), filtered and evaporated to an oil in vacuo. Chromatography on silica eluting with acetone/hexane [1:2] then gave the title compound (0.22 g) as a foam.

MS (FAB): 888.43 [M+Rb]+

$^{13}$C NMR (CDCl$_3$) δ: (Major rotamer) 212.4 (C16); 196.1 (C2); 168.9 (C10); 164.6 (C3); 138.8 (C19); 135.4 (C41); 132.3 (C29); 128.9 (C31); 122.3 (C18); 116.4 (C42); 96.8 (C1); 81.9 (C34); 77.4 (C12); 75 (C23); 73.5 (C25); 72.7 (C24); 56.8 (C9); 52.7 (C17); 48.4 (C 20); 43.3 (C15); 39.6 (C13); 39.1 (C5); 35.6 (C21); 34.6 (C27); 30.4 (C32); 20.9 (C7); 20.2 (C44); 13.7 (C30); 9.4 (C39).

EXAMPLE 40

1,14-Dihydroxy-12-[2-(4(S)-hydroxy-3-methoxycyclohexyl)-1-methylvinyl]-23,25-dimethoxy-17-ethyl-13,19,21,27-tetra methyl-11,28-dioxa-4-azatricyclo[22.3.1.0$^{4,9}$]octacos-18-ene-2.3,10.16-tetraone a)

1-Hydroxy-12-[2-(4(S)-hydroxy-3-methoxycyclohexyl)-1-methylvinyl]-14-$^t$butyldimethylsilyloxy-23,25-dimethoxy-17-ethyl-13,19,21,27-tetramethyl-11,28-dioxa-4-azatricyclo [22.3.1.0$^{4,9}$]octacos-18-ene-2.3,10,16-tetraone Using the method of Example 39(a)-(d) the subtitle compound was prepared from 1,14-dihydroxy-12-[2-(4-hydroxy-3-methoxy cyclohexyl)-1-methylvinyl]-23,25-dimethoxy-17-ethyl-13,19,21,27-tetramethyl-11,28-dioxa-4-azatricyclo (22.3.1.0$^{4,9}$]octacos-18-ene-2,3,10,16-tetraone (FR-900520) .

b)
1,14-Dihydroxy-12-[2-(4(S)-hydroxy-3-methoxycyclohexyl)
-1-methylvinyl]-23,25-dimethoxy-17-ethyl-13,19,21,27-tetramethyl-11,28-dioxa-4-azatricyclo[22.3.1.0^{4,9}]octacos-18-ene-2.3,10,16-tetraone Using the method of Example 39(e) the title compound was prepared from the product of step (a).
MS (FAB): 876 [M+Rb]+

EXAMPLE 41

1,14-dihydroxy-12-[2-(4(S)-hydroxy-3-methoxycyclohexyl)-1-methylvinyl]-23,25-dimethoxy-17-propyl-13,19,21,27-tetra
methyl-11-28-dioxa-4-azatricyclo[22.3.1.0^{4,9}]octacos-18-ene-2.3,10,16-tetraone To a solution of the product of Example 39 (20 mg) in methanol (10 ml) was added 10% Pd-on-C (5 mg) and the resulting suspension was then stirred in an atmosphere of hydrogen for 2 hours at 0° C. The reaction mixture was then filtered and volatiles were removed in vacuo. Chromatography on silica then gave the title compound as a foam (16 mg).
MS (FAB): 890 [M+Rb]+

EXAMPLE 42

17-Allyl-1,14-dihydroxy-12-[2-(4-iodo-3-methoxycyclohexyl)
-1-methylvinyl]-23,25-dimethoxy-13,19,21,27-tetramethyl-11,28-dioxa-4-azatricyclo[22.3.1.0^{4,9}]octacos-18-ene-2.3,10,16-tetraone a)
17-Allyl-1-hydroxy-12-[2-(4-iodo-3-methoxycyclohexyl)
-1-methylvinyl]-14-^tbutyldimethylsilyloxy-23,25-dimethoxy-13,19,21,27-tetramethyl-11,28-dioxa-4-azatricyclo[22.3.1.0^{4,9}]octacos-18-ene-2.3,10,16-tetraone To a stirred, cold (−20° C.) solution of the product of Example 39(d) (0.1 g) in dry distilled dichloromethane (5 ml) containing dry pyridine (0.4 ml) under nitrogen was added trifluoromethanesulphonic anhydride (0.3 ml). After 20 minutes at −20° C. 2 ml of saturated aqueous sodium hydrogen carbon ate solution was added and the reaction mixture was extracted with diethyl ether. The organic extracts were then washed with saturated aqueous sodium hydrogen carbonate solution, dilute aqueous hydrochloric acid (1N) and saturated aqueous sodium hydrogen carbonate solution before being dried (MgSO4), filtered and concentrated to an oil in vacuo. This was taken up in dry benzene (10 ml) containing triethylamine (0.1 ml) and was heated under reflux for one hour. Tetra-^nbutylammonium iodide (200 mg) was then added and heating was continued for a further 30 minutes. The reaction mixture was then cooled and poured into ether. The separated ether layer was washed with dilute aqueous hydrochloric acid (1N), saturated aqueous sodium hydrogen carbonate, sodium thiosulphate solution and brine, before being dried (MgSO4), filtered and evaporated to an oil in vacuo. Chromatography on silica eluting with hexane in an increasing acetone gradient gave the subtitle compound (30 mg) as a foam.

b)
17-Allyl-1,14-dihydroxy-12-[2-(4-iodo-3-methoxycyclohexyl)-1-methylvinyl]-23,25-dimethoxy-13,19,21,27-tetra
methyl-11,28-dioxa-4-azatricyclo[22.3.1.0^{4,9}]octacos-18-ene-2.3,10,16-tetraone To a solution of the product of step (a) (30 mg) in acetonitrile (7 ml) was added 40% aqueous hydrofluoric acid (1 ml). After stirring for 1 hour at room temperature the reaction mixture was poured into saturated aqueous sodium hydrogen carbonate solution and the mixture was extracted with diethyl ether. The combined ether extracts were then washed with saturated aqueous sodium hydrogen carbonate solution and brine before being dried (MgSO4), filtered and concentrated to an oil in vacuo. Chromatography on silica eluting with acetone/hexane [1:4] then gave the title compound (17 mg) as a foam.
MS (FAB): 870.74 [M-I+Rb]+; 997.15 [M+Rb]+
$^{13}$C NMR (CDCl$_3$) δ: (Major rotamer) 213 (C16); 196.3 (C2) 169.1 (C10); 164.8 (C3); 139.0 (C19); 135.7 (C41); 132.8 (C29); 129.1 (C31); 122.4 (C18); 116.7 (C18); 97 (C1); 78.9 (C34); 76.6 (C12); 75.2 (C23); 73.8 (C25); 73.0 (C24); 70.2 (C14); 56.7 (C9); 52.8 (C17); 26.3 (C21); 9.4 (C39).

EXAMPLE 43

17-Allyl-1,14-dihydroxy-12-[2-(3-methoxycyclohexyl)-1-methylvinyl]-23,25-dimethoxy-13,19,21,27-tetramethyl-11,28-dioxa-4-azatricyclo[22.3.1.0^{4,9}]octacos-18-ene-2.3,10,16-tetraone a) 17-Allyl-1-hydroxy-12-[2-(4-(imidazol-1-yl (thiocarbonyl)oxy)-3-methoxycyclohexyl)-1-methylvinyl]-14-^tbutyldimethylsilyloxy-23,25-dimethoxy-13,19,21,27-tetramethyl-11,28-dioxa-4-azatricyclo[22.3.1.0^{4,9}]octacos-18-ene-2.3,10,16-tetraone A solution of the product of Example 39(b) (280 mg) in dry distilled dichloroethane (40 ml) containing 1,1'-thiocarbonyldiimidazole (2 g) was heated under reflux for 36 hours under an atmosphere of nitrogen. Volatiles were then removed in vacuo and the residue was chromatographed on silica eluting with dichloromethane/acetone [9:1] to give the subtitle compound (105 mg) as a foam.

b)
17-Allyl-1.2-dihydroxy-12-[2-(3-methoxycyclohexyl)-1-methylvinyl]-14-^tbutyldimethylsilyloxy-23,25-dimethoxy-13,19,21.27-tetramethyl-11,28-dioxa-4-azatricyclo [22.3.1.0^{4,9}]octacos-18-ene-3,10,16-trione A solution of the product of step (a) (105 mg) in dry benzene (25 ml) containing AIBN (2,2'-bisisobutyronitrile) (3 mg) was heated to 40° C. under nitrogen. Tributyltin hydride (0.1 ml) was then added dropwise by syringe. The temperature was then raised to 60° C. over 5 minutes and a further 0.1 ml of tributyltin hydride was added. The temperature was then further raised to 90° C. over 10 minutes and an additional 0.1 ml of tributyltin hydride was added. After a further 10 minutes no starting material remained and volatiles were removed in vacuo after cooling to room temperature. Chromatography on silica then gave the subtitle compound as an oil (85 mg).

c)

17-Allyl-1-hydroxy-12-[2-(3-methoxycyclohexyl)-1-methylvinyl]-14-('butyldimethylsilyloxy-23,25-dimethoxy-13,19,21,27-tetramethyl-11,28-dioxa-4-azatricyclo [22.3.1.0$^{4,9}$]octacos-18-ene-2.3,10,16-tetraone A solution of the product of step (b) (85 mg) in glacial acetic acid (10 ml) containing copper (II) acetate (1 g) was heated at 80° C. for 5 minutes. The cooled reaction mixture was then poured into saturated aqueous sodium hydrogen carbonate solution and this was extracted with diethyl ether. The ether extracts were then dried (MgSO$_4$), filtered and concentrated to an oil in vacuo. Chromatography on silica eluting with acetone/hexane [2:5] then gave the subtitle compound as a foam (40 mg).

d)

17-Allyl-1,14-dihydroxy-12-[2-(3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone To a solution of the product of step (c) (40 mg) in acetonitrile (8 ml) was added 40% aqueous hydrofluoric acid (1 ml). After stirring for 1 hour at room temperature the reaction mixture was poured into saturated aqueous sodium hydrogen carbonate solution and the mixture was extracted with diethyl ether. The ether extracts were then dried (MgSO$_4$), filtered and concentrated to an oil in vacuo. Chromatography on silica eluting with hexane in an increasing acetone gradient then gave the title compound as a foam (20 mg).

MS (plasma spray): 752.73 (M+H-2H$_2$O]$^+$; 770.76 [M+H-H$_2$O]$^+$; 788.77 [M+H]$^+$; 805.79 [M+NH$_4$]$^+$ $^{13}$C NMR (CDCl$_3$) δ: (Major rotamer) 212.9 (C16); 196.2 (C2); 169 (C10); 164.7 (C3); 139.0 (C19); 135.6 (C41); 131.6 (C29); 130.5 (C31); 122.4 (C18); 116.7 (C42); 97 (C1); 78.9 (C34); 77 (C12); 75.2 (C23); 73.7 (C25); 72.8 (C24); 70.1 (C14); 56.4 (C9); 52.7 (C17); 48.5 (C20); 43.1 (C15); 39.7 (C13); 39.2 (C5); 26.3 (C21); 21.2 (C7); 20.5 (C44); 14.1 (C30); 9.4 (C39).

EXAMPLE 44

1,14-dihydroxy-12-[2-(3-methoxycyclohexyl)-1-methylvinyl]-23,25-dimethoxy-17-ethyl-13,19,21,27-tetramethyl-11,28-dioxa-4-azatricyclo[22.3.1.0$^{4,9}$]octacos-18-ene-2.3,10,16-tetraone a)

1-Hydroxy-12-[2-(4-hydroxy-3-methoxycyclohexyl)-1-methylvinyl]-14-('butyldimethylsilyloxy-23,25-dimethoxy-17-ethyl-13,19,21,27-tetramethyl-11,28-dioxa-4-azatricyclo [22.3.1.0$^{4,9}$]octacos-18-ene-2.3,10,16-tetraone The subtitle compound was prepared from 1,14-dihydroxy-12-[2-(4-hydroxy-3-methoxycyclohexyl)-1-methylvinyl]-23,25-dimethoxy-17-ethyl-13,19,21,27-tetramethyl-11,28-dioxa-4-azatricyclo[22.3.1.0$^{4,9}$]octacos-18-ene-2,3,10,16-tetraone (FR-900520) following the method of Example 5(a) and 39(b).

b)

1,14-dihydroxy-12-[2-(3-methoxycyclohexyl)-1-methylvinyl]-23,25-dimethoxy-17-ethyl-13,19,21,27-tetramethyl-11,28-dioxa-4-azatricyclo[22.3.1.0$^{4,9}$]octacos-18-ene-2.3,10,16-tetraone The title compound was prepared from the product of step (a) following the method of Example 43.
MS (plasma spray): 794 [M+NH$_4$]$^+$

EXAMPLE 45

1,14-dihydroxy-12-[2-(3-methoxycyclohexyl)-1-methylvinyl]-23,25-dimethoxy-17-propyl-13.19.21.27-tetramethyl-11,28-dioxa-4-azatricyclo[22.3.1.0$^{4,9}$]octacos-18-ene-2.3,10,16-tetraone To a solution of the product of Example 43 (28 mg) in methanol (10 ml) was added 10% Pd-on-C (5 mg) and the resulting suspension was then stirred in an atmosphere of hydrogen for 2 hours at 0° C. The reaction mixture was then filtered and volatiles were removed in vacuo. Chromatography on silica then gave the title compound as a foam (25 mg).

MS (plasma spray): 808 [M+NH$_4$]$^+$

EXAMPLE 46

17-Allyl-1-hydroxy-12-[2-(3-methoxycyclohexyl)-1-methyl vinyl]-23,25-dimethoxy-13,19,21,27-tetramethyl-11,28-dioxa-4-azatricyclo[22.3.1.0$^{4,9}$]octacos-18-ene-2.3,10,16-tetraone The title compound was prepared from 17-allyl-1-hydroxy-12-[2-(4-hydroxy-3-methoxycyclohexyl)-1-methylvinyl)-23,25-dimethoxy-13,19,21,27-tetramethyl-11,28-dioxa-4-azatricyclo [22.3.1.0$^{4,9}$]octacos-18-ene-2,3,10,16-tetraone (Example 17, WO 89/05304) following the method of Example 43.

EXAMPLE 47

1-Hydroxy-12-[2-(3-methoxycyclohexyl)-1-methylvinyl]-23,25-dimethoxy-17-propyl-13,19,21,27-tetramethyl-11,28-dioxa-4-azatricyclo[22.3.1.0$^{4,9}$]octacos-18-ene-2.3,10,16-tetraone The title compound was prepared from 1-hydroxy-12-(2-(4-hydroxy-3-methoxycyclohexyl)-1-methylvinyl]-23,25-dimethoxy-17-propyl-13,19,21,27-tetramethyl-11,28-dioxa-4-azatricyclo[22.3.1.0$^{4,9}$]octacos-18-ene-2,3,10,16-tetraone (Example 12, WO 89/05304) following the method of Example 43.

EXAMPLE 48

1-hydroxy-12-[2-(3-methoxycyclohexyl)-1-methylvinyl]-23,25-dimethoxy-17-ethyl-13,19,21,27-tetramethyl-11,28-dioxa-4-azatricyclo[22.3.1.0$^{4,9}$]octacos-18-ene-2.3,10,16-tetraone a)

17-Ethyl-1-hydroxy-12-[2-(4-hydroxy-3-methoxycyclo hexyl)-1-methylvinyl]-23,25-dimethoxy-13,19,21,27-tetra methyl-11,28-dioxa-4-azatricyclo[22.3.1.0$^{4,9}$]octacos-14,18-diene-2.3,10,16-tetraone 17-Ethyl-1,14-dihydroxy-12-[2-(4-hydroxy-3-methoxycyclo hexyl)-1-methylvinyl)-23,25-dimethoxy-13,19,21,27-tetra methyl-11,28-dioxa-4-azatricyclo(22.3.1.0$^{4,9}$]octacos-18-ene-2,3,10,16-tetraone (FR-900520) (100 mg) and p-toluenesulphonic acid (2 mg) were dissolved in dry toluene (20 ml) and were heated for 2 hours at 100° C. under an atmosphere of nitrogen. Removal of solvent in vacuo and chromatography on silica eluting with hexane/acetone [2:1] gave the subtitle compound as a foam (80 mg).

MS (FAB): 774.8 [M+H]$^+$; 796.85 [M+Na]$^+$; 858.71 [M+Rb]$^+$.

$^{13}$C NMR δ: (major rotamer) 201.15 (C16); 196.0 (C2); 169.2 (C10); 165.1 (C3); 147.8 (C15); 138.0 (C19); 123.82 (C18); 97.88 (C1); 84.05 (C34).

b)
17-Ethyl-1-hydroxy-12-[2-(4-hydroxy-3-methoxycyclohexyl-1-methylvinyl]-23,25-dimethoxy-13,19,21,27-tetramethyl-11,28-dioxa-4-azatricyclo [22.3.1.0$^{4,9}$]octacos-18-ene-2.3,10,16-tetraone A sample of the product from step (a) was dissolved in methanol (20 ml) and 10% Pd-on-carbon (10 mg) was added. The mixture was stirred in an atmosphere of hydrogen for 1.5 hours at room temperature and pressure, and was then filtered through celite and evaporated to an oil in vacuo. Column chromatography on silica eluting with hexane/acetone [2:1] gave the title compound as a foam (50 mg).

MS (FAB): 776 [M+H]$^+$; 798 [M+Na]$^+$; 860 [M+Rb]$^+$.

$^{13}$C NMR δ: (major rotamer) 212.34 (C16); 196.42 (C2); 169.38 (C10); 165.16 (C3); 138.9 (C19); 124.16 (C18); 97.41 (C1); 84.19 (C34).

c)
1-Hydroxy-12-[2-43-methoxycyclohexyl)-1-methylvinyl]-23,25-dimethoxy-17-ethyl-13,19,21,27-tetramethyl-11,28-dioxa-4-azatricyclo[22.3.1.0$^{4,9}$]octacos-18-ene-2.3,10,16-tetraone The title compound was prepared from the product of step (b) following the method of Example 43.

EXAMPLE 49

17-Allyl-1.14-dihydroxy-12-[2-(cyclohex-3-enyl)-1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone a)
17-Allyl-1-hydroxy-12-[2-(4-iodo-3-methoxycyclohexyl)
-1-methylvinyl]-14-$^t$butyldimethylsilyloxy-23,25-dimethoxy-13,19,21,27-tetramethyl-11,28-dioxa-4-azatricyclo [22.3.1.0$^{4,9}$]octacos-18-ene-2,3,10,16-tetraone To a stirred, cold (−20° C.) solution of 17-allyl-1-hydroxy-12-[2-(4S)-hydroxy-3-methoxycyclohexyl)-1-methylvinyl]-14-$^t$butyldimethylsilyloxy-23,25-dimethoxy-13,19,21,27-tetramethyl-11,28-dioxa-4-azatricyclo(22.3.1.0$^{4,9}$]octacos-18-ene-2,3,10,16-tetraone [the product of Example 39(d)] (0.54 g) in dry distilled dichloromethane (25 ml) containing dry pyridine (2 ml) under nitrogen was added trifluoromethanesulphonic anhydride (1.2 ml). After 20 minutes at −20° C. 10 ml of saturated aqueous sodium hydrogen carbonate solution was added and the reaction mixture was extracted with diethyl ether. The organic extracts after washing with saturated aqueous sodium hydrogen carbonate solution, dilute aqueous hydrochloric acid (1N) and saturated aqueous sodium hydrogen carbonate solution were dried (MgSO$_4$), filtered and concentrated to an oil in vacuo. This was taken up in dry benzene (30 ml) containing dry pyridine (0.3 ml) and tetra-$^n$butylammonium iodide (1.0 g) was added. After heating for 30 minutes under reflux the reaction mixture was cooled to room temperature and poured into ether. The separated ether layer was washed with dilute aqueous hydrochloric acid (1N), saturated aqueous sodium hydrogen carbonate, sodium thiosulphate solution and brine, before being dried (MgSO$_4$), filtered and evaporated to an oil in vacuo. Chromatography on silica eluting with acetone/hexane [1:4] then gave the title compound (500 mg) as a diastereoisomeric mixture of iodides. (A smaller scale synthesis of the subtitle compound was described in Example 42(a)].

b)
17-Allyl-1.2-dihydroxy-12-[2-(cyclohex-3-enyl)-1-methylvinyl]-14-$^t$butyldimethylsilyloxy-23-25-dimethoxy-13,19,21,27-tetramethyl-11,28-dioxa-4-azatricyclo [22.3.1.0$^{4,9}$]octacos-18-ene-3,10,16-trione To a solution of the product of step (a) (500 mg) in glacial acetic acid (8 ml) was added zinc dust. After stirring for 10 minutes at room temperature the reaction mixture was poured into saturated aqueous sodium hydrogen carbonate solution and this was extracted with diethyl ether. The ether extracts were then washed with saturated aqueous sodium hydrogen carbonate solution, dilute aqueous hydrochloric acid (1N) and saturated aqueous sodium hydrogen carbonate solution before being dried (MgSO$_4$), filtered and concentrated in vacuo to give the subtitle compound (320 mg) as an oil.

c)
17-Allyl@-hydroxy-12-[2-(cyclohex-3-enyl)-1-methylvinyl]-14-$^t$butyldimethylsilyloxy-23,25-dimethoxy-13,19,21,27-tetramethyl-11,28-dioxa-4-azatricyclo [22.3.1.0$^{4,9}$]octacos-18-ene-2-3,10,16-tetraone A solution of the product of step (b) (320 mg) in glacial acetic acid (8 ml) containing copper (II) acetate was heated at 85° C. for 5 minutes. After cooling to room temperature the reaction mixture was poured into saturated aqueous sodium hydrogen carbonate solution and this was then extracted with diethyl ether. The organic extract after washing with saturated aqueous sodium hydrogen carbonate solution, dilute aqueous hydrochloric acid (1N) and saturated aqueous sodium hydrogen carbonate solution was dried (MgSO$_4$), filtered and concentrated to an oil in vacuo. Chromatography on silica eluting with hexane in an increasing acetone gradient then gave the title compound as a foam (280 mg).

d)
17-Allyl-1,14-dihydroxy-12-[2-(cyclohex-3-enyl)-1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone To a solution of the product from step (c) (280 mg) in acetonitrile (20 ml) was added 40% aqueous hydrofluoric acid (4 ml). After stirring for 30 minutes at room temperature the reaction mixture was poured into saturated aqueous sodium hydrogen carbonate solution and the mixture was extracted with diethyl ether. The combined ether extracts after washing with saturated aqueous sodium hydrogen carbonate solution were then dried (MgSO$_4$), filtered and concentrated to an oil in vacuo. Chromatography on silica eluting with hexane in an increasing acetone gradient then gave the title compound as a foam (0.227 g).

MS (plasma spray): 720.52 [M+H-2H$_2$O]$^+$; 738.50 [M+H-H$_2$O]$^+$; 756.58 [M+H]$^+$; 773.53 [M+NH$_4$]$^+$ MS (FAB): 840.81 [M+Rb]$^+$ $^{13}$C NMR δ: (Major rotamer) 212.5 (C16); 196.2 (C2); 168.9 (C10); 164.6 (C3); 138.8 (C19); 135.5 (C40); 131.4 (C31); 131.2 (C29); 126.9 (C34); 125.9 (C35); 122.4 (C18); 116.5 (C41); 96.9 (C1); 77.4 (C12); 76.5 (C23); 73.5 (C25); 72.7 (C24); 69.9 (C14); 56.5 (C9); 52.7 (C17); 48.5 (C20); 43.4 (C15); 26.1 (C21); 20.3 (C43); 13.8 (C30); 9.4 (C38).

EXAMPLE 50

1,14-Dihydroxy-12-[2-(cyclohex-3-enyl)-1-methylvinyl]-23,25-dimethoxy-17-ethyl-13,19,21,27-tetramethyl-11,28-dioxa-4-azatricyclo[22.3.1.0$^{4,9}$]octacos-18-ene-2.3,10,16-tetraone The title compound was prepared from the subtitle compound of Example 40(a) using the method of Example 49.
MS (FAB): 829 [M+Rb]+.

EXAMPLE 51

1,14-dihydroxy-12-[2-(cyclohex-3-enyl)-1-methylvinyl]-23.25-dimethoxy-17-propyl-13,19,21,27-tetramethyl-11,28-dioxa-4-azatricyclo[22.3.1.0$^{4,9}$]octacos-18-ene-2.3,10,16-tetraone a)

1-Hydroxy-12-[2-(4(S)-hydroxy-3-methoxycyclohexyl)-1-methylvinyl]-14-*t*butyldimethylsilyloxy-23,25-dimethoxy-17-propyl-13,19,21,27-tetramethyl-11,28-dioxa-4-azatricyclo
[22.3.1.0$^{4,9}$]octacos-18-ene-2.3,10,16-tetraone The subtitle compound was prepared from 1,14-dihydroxy-12-[2-(4-hydroxy-3-methoxycyclohexyl)-1-methylvinyl)-23,25-dimethoxy-17-propyl-13,19,21,27-tetramethyl-11,28-dioxa-4-azatricyclo[22.3.1.0$^{4,9}$]octacos-18-ene-2,3,10,16-tetraone (Example 10, WO 89/05304) following the method of Example 39(a)–(d).

b)

1,14-dihydroxy-12-[2-(cyclohex-3-enyl)-1-methylvinyl]-23,25-dimethoxy-17-propyl-13,19,21,27-tetramethyl-11,28-dioxa-4-azatricyclo[22.3.1.0$^{4,9}$]octacos-18-ene-2.3,10,16-tetraone The title compound was prepared from the product of step (a) following the method of Example 49.
MS (FAB): 843 [M+Rb]+

EXAMPLE 52

17-Allyl-1-hydroxy-12-[2-(cyclohex-3-enyl)-1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone (a)

17-Allyl-1-hydroxy-12-[2-(4(S)-hydroxy-3-methoxycyclohexyl)-1-methylvinyl]-23,25-dimethoxy-3,19,21,27-tetramethyl-11,28-dioxa-4-azatricyclo
[22.3.1.0$^{4,9}$]octacos-18-ene-2.3,10,16-tetraone The subtitle compound was prepared from 17-allyl-1-hydroxy-12-[2-(4-hydroxy-3-methoxycyclohexyl)-1-methylvinyl]-23,25-dimethoxy-13,19,21,27-tetramethyl-11,28-dioxa-4-aza tricyclo[22.3.1.0$^{4,9}$]octacos-18-ene-2,3,10,16-tetraone (Example 17, WO 89/05304) following the method of Example 39(a)–(d).

(b)

17-Allyl-1-hydroxy-12-[2-(cyclohex-3-enyl)-1-methylvinyl]-23,25-dimethoxy-13,19,21,27-tetramethyl-11,28-dioxa-4-azatricyclo[22.3.1.0$^{4,9}$]octacos-18-ene-2.3,10,16-tetraone The title compound was prepared from the product of step (a) following the method of Example 49(a)–(c).

EXAMPLE 53

1-Hydroxy-12-[2-(cyclohex-3-enyl)-1-methylvinyl]-23,25-dimethoxy-17-ethyl-13,19,21,27-tetramethyl-11,28-dioxa-4-azatricyclo[22.3.1.0$^{4,9}$]octacos-18-ene-2.3,10,16-tetraone a)

1-Hydroxy-12-[2-(4(S)-hydroxy-3-methoxycyclohexyl)-1-methylvinyl]-23,25-dimethoxy-17-ethyl-13,19,21,27-tetramethyl-11,28-dioxa-4-azatricyclo[22.3.1.0$^{4,9}$]octacos-8-ene-2.3,10,16-tetraone The subtitle compound was prepared from 1-hydroxy-2-[2-(4-hydroxy-3-methoxycyclohexyl)-1-methylvinyl]-23,25-dimethoxy-17-ethyl-13,19,21,27-tetramethyl-11,28-dioxa-4-aza tricyclo[22.3.1.0$^{4,9}$]octacos-18-ene-2,3,10,16-tetraone [the product of Example 48(b)] following the method of Example 39(a)–(d).
MS (FAB) : 861 [M+Rb]+ b)

1-Hydroxy-12-[2-(cyclohex-3-enyl)-1-methylvinyl-23,25-dimethoxy-17-ethyl-13,19,21,27-tetramethyl-11,28-dioxa-4-azatricyclo[22.3.1.0$^{4,9}$]octacos-18-ene-2.3,10,16-tetraone The title compound was prepared from the product of step (a) following the method of Example 49(a)–(c).

EXAMPLE 54

1-Hydroxy-12-[2-(cyclohex-3-enyl)-1-methylvinyl]-23,25-dimethoxy-17-propyl-13,19,21,27-tetramethyl-11,28-dioxa-4-azatricyclo[22.3.1.0$^{4,9}$]octacos-18-ene-2.3,10,16-tetraone a)

1-Hydroxy-12-[2-(4-trifluoromethylsulphonyloxy-3-methoxycyclohexyl)-1-methylvinyl]-23,25-dimethoxy-17-propyl-13,19,21,27-tetramethyl-11,28-dioxa-4-azatricyclo [22.3.1.0$^{4,9}$]octacos-18-ene-2.3,10,16-tetraone To a cold (−10° C.) stirred solution of 1-hydroxy-12-(2-(4-hydroxy-3-methoxycyclohexyl)-1-methylvinyl]-23,25-dimethoxy-17-propyl-13,19,21,27-tetramethyl-11,28-dioxa-4-azatricyclo(22.3.1.0$^{4,9}$)octacos-18-ene-2,3,10,16-tetraone (Example 12, WO 89/05304) (0.3 g) in dry dichloromethane (12 ml) under nitrogen was added trifluoromethanesulphonic anhydride (0.1 ml) until no starting material remained. Saturated aqueous sodium hydrogen carbonate solution was then added and the reaction mixture was extracted with diethyl ether. The ether extracts, after washing with saturated aqueous sodium hydrogen carbonate solution, dilute aqueous hydrochloric acid (1N), and saturated aqueous sodium hydrogen carbonate solution, were dried (MgSO$_4$), filtered and concentrated in vacuo to give the subtitle compound as an oil (300 mg).

b)

1-Hydroxy-12-[2-(4(S)-hydroxy-3-methoxycyclohexyl)-1-methylvinyl]-23,25-dimethoxy-17-propyl-13,19,21,27-tetramethyl-11,28-dioxa-4-azatricyclo[22.3.1.0$^{4,9}$]octacos-18-ene-2.3,10,16-tetraone Silica (18 g, Merck Kieselgel 60) was added to a solution of the product of step (a) (300 mg) in dichloromethane (100 ml). Volatiles were then removed in vacuo at room temperature and the resulting freely flowing powder was stored at 8° C. for 16 hours. The support was then washed with acetone containing triethylamine and the solvent was evaporated in vacuo to an oil. Chromatography on silica eluting with hexane in an acetone gradient then gave the title compound as a foam (79 mg).

MS (FAB): 772.83 $[M+H-H_2O]^+$; 812.85 $[M+Na]^+$; 874.65 $[M+Rb]^+$ $^{13}$C NMR (CDCl$_3$) δ: (Major rotamer) 212.2 (C16); 196.2 (C2); 169.2 (C10); 165.1 (C3); 138.0 (C19); 131.3 (C29); 130.2 (C31); 124.1 (C18); 97.2 (C1); 75.3 (C23); 69 (C35); 56.1 (C9); 53.4 (C17); 49.1 (C20); 37.7 (C5); 34.9 (C13); 34.5 (C27); 30.5 (C32); 26.3 (C21); 20.8 (C7); 20.3 (C41).

c)

1-Hydroxy-12-[2-(cyclohex-3-enyl)-1-methylvinyl]-23,25-dimethoxy-17-propyl-13,19,21,27-tetramethyl-11,28-dioxa-4-azatricyclo[22.3.1.0$^{4,9}$]octacos-18-ene-2.3,10,16-tetraone The title compound was prepared from the product of step (a) following the method of Example 49(a)–(c).

EXAMPLE 55

1,14-Dihydroxy-12-(2-cyclohexyl-1-methylvinyl)-23,25-dimethoxy-17-propyl-13.19,21,27-tetramethyl-11,28-dioxa-4-azatricyclo[22.3.1.0$^{4,9}$]octacos-18-ene-2.3,10,16-tetraone To a solution of the product of Example 49 (60 mg) in dry methanol (12 ml) was added 10% Pd-on-C (100 mg) and the resulting suspension was stirred in an ice bath for one hour under an atmosphere of hydrogen. The reaction mixture was then filtered and concentrated to an oil in vacuo. Chromatography on silica eluting with hexane in an increasing acetone gradient then gave the title compound as a foam (44 mg).

MS (plasma spray): 724.56 $[M+H-2H_2O]^+$; 742.54 $[M+H-H_2O]^+$; 760.63 $[M+H]^+$; 777.61 $[M+NH_4]^+$ MS (FAB): 844.86 $[M+Rb]^+$ $^{13}$C NMR (CDCl$_3$) δ: (Major rotamer) 213.1 (C16); 195.9 (C2); 168.7 (C10); 164.4 (C3); 138.0 (C19); 131.9 (C31); 130.3 (C29); 123 (C18); 96.7 (C1); 74.9 (C23); 73.3 (C25); 72.5 (C24); 69.8 (C14); 56.3 (C9); 52.6 (C17); 48.3 (C20); 43.1 (C15); 39.3 (C13); 38.8 (C5); 36.2 (C32); 34.2 (C27); 20.1 (C43); 9.2 (C38).

EXAMPLE 56

1,14-Dihydroxy-12-[2-cyclohexyl-1-methylvinyl]-23.25-dimethoxy-17-ethyl-13.19,21,27-tetramethyl-11,28-dioxa-4-azatricyclo[22.3.1.0$^{4,9}$]octacos-18-ene-2.3,10,16-tetraone To a solution of the product of Example 50 (15 mg) in dry methanol (4 ml) was added 104 Pd-on-C (6 mg) and the resulting suspension was stirred in an ice bath for one hour under an atmosphere of hydrogen. The reaction mixture was then filtered and concentrated to an oil in vacuo. Chromatography on silica eluting with hexane in an increasing acetone gradient then gave the title compound as a foam (14 mg).

MS (FAB): 831 $[M+Rb]^+$

EXAMPLE 57

1-Hydroxy-12-[2-cyclohexyl-1-methylvinyl]-23.25-dimethoxy-17-ethyl-13,19,21,27-tetramethyl-11,28-dioxa-4-azatricyclo [22.3.1.0$^{4,9}$]octacos-18-ene-2.3,10,16-tetraone The title compound was prepared from the product of Example 53 following the method of Example 55.

EXAMPLE 58

1-Hydroxy-12-[2-cyclohexyl-1-methylvinyl]-23,25-dimethoxy-17-propyl-13,19,21,27-tetramethyl-11,28-dioxa-4-azatricyclo [22.3.1.0$^{4,9}$]octacos-18-ene-2.3,10,16-tetraone The title compound was prepared from the product of Example 54 following the method of Example 55.

EXAMPLE 59

17-Allyl-1,14-dihydroxy-12-[2-(3-methoxycyclohexyl)-1-methylvinyl]-23-25-dimethoxy-13,19,21,27-tetramethyl-11,28-dioxa-4-azatricyclo[22.3.1.0$^{4,9}$]octacos-18-ene-3,10,16-trione a)

17-Allyl-1-hydroxy-12-[-2-(4-$^t$butyldimethylsilyloxy-3-methoxy cyclohexyl)-1-methylvinyl]-14-$^t$butyldimethylsilyloxy-23,25-dimethoxy-13-19,21,27-tetramethyl-11,28-dioxa-4-azatricyclo[22.3.1.0$^{4,9}$]octacos-18-ene-2.3,10,16-tetraone To a cold (0° C.) stirred solution of FR-900506 (1 g) in dry dichloromethane (25 ml) containing 2,6-dimethylpyridine (5 ml) under nitrogen was added $^t$butyldimethylsilyltriflate (2 ml) until all the starting material had disappeared. The reaction mixture was then quenched with water and, after stirring for 5 minutes at room temperature, was extracted with diethyl ether. The ether extracts after washing with dilute aqueous hydrochloric acid (1N)(×2), saturated aqueous sodium hydrogen carbonate solution and brine were dried (MgSO$_4$), filtered and concentrated in vacuo to give the subtitle compound as an oil (1.28 g).

b)

17-Allyl-1-hydroxy-12-[2-(4-hydroxy-3-methoxycyclohexyl)-1-methylvinyl]-14-$^t$butyldimethyl silyloxy-23,25-dimethoxy-13,19,21.27-tetramethyl-11,28-dioxa-4-azatricyclo[22.3.1.0$^{4,9}$]octacos-18-ene-2.3,10,16-tetraone A solution of the product from step (a) in methanol (100 ml) containing pyridinium p-toluene sulphonate was stirred for 18 hours at room temperature. Volatiles were then removed in vacuo and the residue was dissolved in diethyl ether. The ethereal solution after washing with saturated aqueous sodium hydrogen carbonate solution, dilute aqueous hydrochloric acid (1N), saturated aqueous sodium hydrogen carbonate solution and brine was dried (MgSO$_4$), filtered and evaporated in vacuo to give the subtitle compound as a pale yellow foam (0.97 g).

c) 17-Allyl-1-hydroxy-12-[2-(4-(imidazol-1-yl (thiocarbonyl)oxy)-3-methoxycyclohexyl)-1-methylvinyl]-14-$^t$butyldimethylsilyloxy-23,25-dimethoxy-13,19,21,27-tetrameth3il-11,28-dioxa-4-azatricyclo[22.3,1.0$^{4,9}$]octacos-18-ene-2.3,10,16-tetraone A solution of the product of step (b) (280 mg) in dry distilled dichloroethane (40 ml) containing 1,1'-thiocarbonyldiimidazole (2 g) was heated under reflux for 36 hours under an atmosphere of nitrogen. Volatiles were then removed in vacuo and the residue was chromatographed on silica eluting with dichloromethane/acetone [9:1] to give the subtitle compound (105 mg) as a foam.

d) 17-Allyl-1.2-dihydroxy-12-[2-(3-methoxycyclohexyl)-1-methylvinyl]-14-'butyldimethylsilyloxy-23,25-dimethoxy-13,19,21,27-tetramethyl-11,28-dioxa-4-azatricyclo [22.3.1.0⁴,⁹]octacos-18-ene-3,10,16-trione A solution of the product of step (c) (105 mg) in dry benzene (25 ml) containing AIBN (2,2'-bisisobutyronitrile) (3 mg) was heated to 40° C. under nitrogen. Tributyltin hydride (0.1 ml) was then added dropwise by syringe. The temperature was then raised to 60° C. over 5 minutes and a further 0.1 ml of tributyltin hydride was added. The temperature was then further raised to 90° C. over 10 minutes and an additional 0.1 ml of tributyltin hydride was added. After a further 10 minutes no starting material remained and volatiles were removed in vacuo after cooling to room temperature. Chromatography on silica then gave the subtitle compound as an oil (85 mg). e) 17-Allyl-1-hydroxy-12-[2-(3-methoxycyclohexyl)-1-methylvinyl]-14-'butyldimethylsilyloxy-23,25-dimethoxy-13,19,21,27-tetramethyl-11,28-dioxa-4-azatricyclo [22.3.1.0⁴,⁹]octacos-18-ene-2.3,10,16-tetraone A solution of the product of step (d) (85 mg) in glacial acetic acid (10 ml) containing copper (II) acetate (1 g) was heated at 80° C. for 5 minutes. The cooled reaction mixture was then poured into saturated aqueous sodium hydrogen carbonate solution and this was extracted with diethyl ether. The ether extracts were then dried (MgSO₄), filtered and concentrated to an oil in vacuo. Chromatography on silica eluting with acetone/hexane [2:5] then gave the subtitle compound as a foam (40 mg).

f) 17-Allyl-1,14-dihydroxy-12-[2-(3-methoxycyclohexyl)-1-methylvinyl]-23,25-dimethoxy-13,19.21,27-tetramethyl-11,28-dioxa-4-azatricyclo[22.3.1.0⁴,⁹]octacos-18-ene-2.3,10,16-tetraone To a solution of the product of step (e) (40 mg) in acetonitrile (8 ml) was added 40% aqueous hydrofluoric acid (1 ml). After stirring for 1 hour at room temperature the reaction mixture was poured into saturated aqueous sodium hydrogen carbonate solution and the mixture was extracted with diethyl ether. The ether extracts were then dried (MgSO₄), filtered and concentrated to an oil in vacuo. Chromatography on silica eluting with hexane in an increasing acetone gradient then gave the subtitle compound as a foam (20 mg).

MS (plasma spray): 752.73 [M+H-2H₂O]⁺; 770.76 [M+H-H₂O]⁺; 788.77 [M+H]⁺; 805.79 [M+NH₄]⁺

¹³C NMR (CDCl₃) δ: (Major rotamer) 212.9 (C16); 196. 2 (C2) 169 (C10) 164. 7 (C3) 139. 0 (C19); 135.6 (C41); 131.6 (C29); 130.5 (C31); 122.4 (C18); 116.7 (C42); 97 (C1); 78.9 (C34); 77 (C12); 75.2 (C23); 73.7 (C25); 72.8 (C24); 70.1 (C14); 56.4 (C9); 52.7 (C17); 48.5 (C20); 43.1 (C15); 39.7 (C13); 39.2 (C5); 26.3 (C21); 21.2 (C7); 20.5 (C44); 14.1 (C30); 9.4 (C39).

g) 17-Allyl-1,14-dihydroxy-12-[2-(3-methoxycyclohexyl)-1-methylvinyl]-23,25-dimethoxy-13,19,21,27-tetramethyl-11,28-dioxa-4-azatricyclo[22.3.1.0⁴,⁹]octacos-18-ene-3,10.16-trione Hydrogen sulphide gas was bubbled through a solution of the product of step (f) (40 mg) in pyridine (2 ml) and dimethylformamide (0.1 ml) for 2 hours at room temperature. After standing for 4 hours at room temperature dilute aqueous hydrochloric acid was added and the reaction mixture was extracted with ethyl acetate. The ethyl acetate extract was then dried (MgSO₄), filtered and concentrated in vacuo. Chromatography on silica eluting with ethyl acetate then gave the title compound as a foam (25 mg).

MS (FAB): 858 (M+Rb)⁺; 796 (M+Na)⁺; 774 (M+H)⁺; 756 (M-OH)⁺

¹³C NMR (CDCl₃) δ: 214.3 (C16); 174 (C3); 169.4 (C10); 141.2 (C19); 135.4 (C41); 131.6 (C29); 129.8 (C31); 121.4 (C18); 116.6 (C42); 97.8 (C1); 78.9 (C34); 48.4 (C20); 20.7 (C7); 14.3 (C30); 9.7 (C39)

EXAMPLE 60

17-Allyl-14-hydroxy-12-[2-(4-hydrogy-3-methoxycyclohexyl)-1-23,25-dimethoxy-13,19,21,27-tetramethyl-11,28-dioxa-4-azatricyclo[22.3.1.0⁴,⁹]octacos-18-ene-2.3,10,16-tetraone and 17-Allyl-14-hydroxy-12-[2-(4-hydroxy-3-methoxycyclohexyl)-1-methylvinyl]-23,25-dimethoxy-1,13,19,21,27-pentamethyl-11,28-dioxa-4-azatricyclo[22.3.1.0⁴,⁹]octacos-18-ene-2-3,10,16-tetraone a) 17-Allyl-1-chloro-14-hydroxy-12-[2-(4-hydroxy-3-methoxycyclohexyl)-1-methylvinyl]-23,25-dimethoxy-13,19,21.27-tetramethyl-11,28-dioxa-4-azatricyclo [22.3.1.0⁴,⁹]octacos-18-ene-2.3,10,16-tetraone A solution of FR-900506 (500 mg) in dry dichloromethane (25 ml) was added dropwise over 1 minute to a stirred, cool (0° C.) solution of thionyl chloride (0.45 ml) and pyridine (1.11 ml) in dry dichloromethane (20 ml) under nitrogen. After 20 minutes, saturated aqueous sodium hydrogen carbonate solution was added and the mixture was stirred at room temperature for 20 minutes. The organic extract was then separated and washed with dilute aqueous hydrochloric acid (1M, 20 ml), water (20 ml) and brine (10 ml) before being dried (MgSO₄), filtered and evaporated in vacuo to give the sub-title compound as an an oil (512 mg).

b) 17-Allyl-14-hydroxy-12-[2-(4-hydroxy-3-methoxycyclo hexyl)-1-methylvinyl]-23.25-dimethoxy-13,19,21,27-tetramethyl-11,28-dioxa-4-azatricyclo[22.3.1.0⁴,⁹]octacos-18-ene-2.3,10,16-tetraone and 17-Allyl-14-hydroxy-12-[2-(4-hydroxy-3-methoxycyclohexyl)-1-methylvinyl]-23,25-dimethoxy-1,13,19,21,27-pentamethyl-1,28-dioxa-4-azatricyclo[22.3.1.0⁴,⁹]octacos-18-ene-2.3,10,16-tetraone To a cold (−50° C.), stirred suspension of copper (I) iodide (463 mg) in dry diethyl ether (20 ml) under nitrogen was added a dilute (1.1M) solution of methyl lithium in ether (4.42 ml). After stirring for 30 minutes at −40° C. the reaction mixture was cooled to −70° C. and a solution of the product from step (a) (400 mg) in dry ether (20 ml) was added dropwise. After stirring for 20 minutes, saturated aqueous ammonium chloride solution was added and the reaction mixture was allowed to warm to room temperature. The ethereal layer was then separated and was washed with water (20 ml) and brine (20 ml) before being dried (MgSO₄), filtered and evaporated to an oil in vacuo. Chromatography on silica then gave a first isomer of the first title compound (Isomer A, 5 mg), a second isomer of the first title compound (Isomer B, 20 mg), and the second title compound (4.5 mg).

MS (FAB):

Isomer A—770.8 [M+H-H₂O]⁺; 788.8 [M+H]⁺; 810.8 [M+Na]⁺; 872.6 [M+Rb]⁺

Isomer B—872.4 [M+Rb]⁺

2nd title compound—784.8 [M+H-H₂O]⁺; 802.8 [M+H]⁺; 824.8 [M+Na]⁺; 886.5 [M+Rb]⁺

¹³C NMR (CHCl₃) δ:

Isomer A—211.4 (C16); 200.7 (C2); 169 (C10); 165.6 (C3) 139.6 (C19) 135.7 (C41); 131.9 (C31); 131.2 (C29); 122.4 (C18); 116.5 (C42); 84.2 (C34); 80.5 (C12); 78.3 (C1); 76.9 (C23); 75.2 (C24); 74.9 (C25); 73.5 (C35); 68.5 (C14); 53.4 (C17); 52 (C9); 47.7 (C20); 45.5 (C15); 44.3 (C5); 40.1 (C13); 35.2 (C40); 34.9 (C32); 34.8 (C22); 34.6 (C33); 32.7 (C26); 31.5 (C27); 31.2 (C36); 30.5 (C37); 27.1 (C21); 25.8 (C8); 24.9 (C6); 20.8 (C7); 20.5 (C44); 17.1 (C43); 16.4 (C47); 13.3 (C30); 10.1 (C39)

Isomer B—213.2 (C16); 197 (C2); 170.2 (C10); 163.8 (C3); 137.3 (C19); 135.2 (C41); 131.9 (C29); 128.5 (C31); 123.4 (C18); 116.7 (C42); 84.1 (C34); 83.5 (C1); 79.3 (C12); 70.2 (C14); 55.9 (C9); 51.9 (C17); 49.4 (C20); 44.7 (C15); 40 (C5); 40.1 (C13); 38.5 (C40); 10.1 (C39)

2nd title compound—212.4 (C16); 203.3 (C2); 169.4 (C10); 167 (C3); 139.1 (C19); 135.6 (C41); 131.8 (C29); 129.7 (C31); 123 (C18); 116.6 (C42); 84.2 (C34); 82.9 (C1); 77.3 (C12); 69.7 (C14); 52.5 (C17); 52 (C9); 47.7 (C20); 45.2 (C15); 44 (C5); 39.9 (C13); 14.1 (C48); 10 (C39).

Isomers A and B differ in their stereochemistry at Cl.

EXAMPLE 61

17-Allyl-1,14-Dihydroxy-12-[2-(cyclopentyl-3-methanol(methyl ether))-1-methylvinyl]-23,25-dimethoxy-13,19,21,27-tetra methyl-11,28-dioxa-4-azatricyclo[22.3.1.0⁴,⁹]octacos-18-ene-2.3,10,16-tetraone To a solution of the compound of Example 10(a) (73 mg) in diethyl ether (2 ml) containing boron trifluoride diethyl etherate (0.1 ml) was added an ethereal solution of diazomethane. After standing for 30 minutes at room temperature volatiles were removed in vacuo and the residue was chromatographed on silica eluting with hexane/acetone [4:1] to give 17-allyl-1-hydroxy-12-(2-(cyclopentyl-3-methanol(methylether))-1-methylvinyl]-23,25-dimethoxy-14-ᵗbutyldimethylsilyloxy-13,19,21,27-tetramethyl-11,28-dioxa -4-azatricyclo[22.3.1.0⁴,⁹]octacos-18-ene-2,3,10,16-tetraone (20 mg) as a foam. This was dissolved in acetonitrile (5 ml) and 40% aqueous hydrofluoric acid (0.5 ml) was then added. After stirring for 75 minutes at room temperature the reaction mixture was poured into ethyl acetate and was washed with saturated aqueous sodium hydrogen carbonate solution and brine before being dried, (MgSO₄), filtered and evaporated to an oil in vacuo. Chromatography on silica eluting with acetone/hexane [1:3] then gave the title compound (10 mg) as a foam.

¹³C NMR (CDCl₃) δ: (Major rotamer) 213.8 (C16); 196.2 (C2); 168.9 (C10); 164.9 (C3); 138.9 (C19); 135.6 (C40); 122.5 (C1S); 116.6 (C41); 97 (C1); 77.4 (C12); 75.2 (C23); 70.1 (C14); 58.8 (cyclopentylCH₂OCH₃); 56.3 (C9); 52.8 (C17); 48.6 (C20); 29.7 (C8); 26.3 (C21); 24.6 (C6); 21.1 (C7); 20.4 (C43); 14.1 (C30); 9.5 (C38)

MS (FAB): 872 [M+Rb]⁺; 810 [M+Na]⁺; 788 [M+H]⁺.

EXAMPLE 62

17-Allyl-1,14-dihydroxy-12-[2-(4-amino-3-methoxycyclohexyl)-1-methylvinyl]-23,25-dimethoxy-13,19,21,27-tetramethyl-11,28-dioxa-4-azatricyclo[22.3.1.0⁴,⁹]octacos-18-ene-2.3,10,16-tetraone a)

17-Allyl-1-hydrogy-12-[2-(4-azido-3-methoxycyclohexyl)-1-methylvinyl]-23,25-dimethoxy-14-ᵗbutyldimethylsilyloxy-13,19,21,27-tetramethyl-3-1,28-dioxa-4-azatricyclo [22.3.1.0⁴,⁹]octacos-18-ene-2.3,10,16-tetraone To a stirred, cold (−20° C.) solution of the product of Example 39(b) (0.19 g) in dry distilled dichloromethane (7 ml) containing dry pyridine (0.63 ml) under nitrogen was added trifluoromethanesulphonic anhydride (0.41 ml). After 20 minutes at −20° C. saturated aqueous sodium hydrogen carbonate solution (3 ml) was added and the reaction mixture was extracted with diethyl ether. The organic extracts were then washed with saturated aqueous sodium hydrogen carbonate solution, dilute aqueous hydrochloric acid (1N), and saturated aqueous sodium hydrogen carbonate solution before being dried (MgSO₄), filtered and concentrated to an oil in vacuo. This material was dissolved in dry DMF (5 ml) and sodium azide (0.5 g) was added. After stirring for 30 minutes at room temperature the reaction mixture was poured into water and this was then extracted with ethyl acetate. The organic extract after washing with brine was dried (MgSO₄), filtered and concentrated to an oil in vacuo. Chromatography on silica then gave the subtitle compound (83 mg) as a foam.

b)

17-Allyl-1-hydroxy-12-[2-(4-amino-3-methoxycyclohexyl)-1-methylvinyl]-23,25-dimethoxy-14-ᵗbutyldimethylsilyloxy-13,19,21,27-tetramethyl-11,28-dioxa-4-azatricyclo [22.3.1.0⁴,⁹]octacos-18-ene-2.3,10,16-tetraone To a stirred solution of the product of step (b) (50 mg) in dry, distilled methanol (5 ml) under nitrogen was added 1,3-propanedithiol (0.03 ml) and triethylamine (0.04 ml). After stirring for 1 hour at room temperature the reaction mixture was columned on silica eluting with hexane/acetone [3:1] to give the subtitle compound as a foam (37 mg).

¹³C NMR (CDCl₃) δ: (Major rotamer) 209.6 (C16); 196.5 (C2); 169.1 (C10); 164.7 (C3); 138.5 (C19); 135.7 (C41); 133.3 (C29); 128.3 (C31); 123.2 (C18); 116.6 (C42); 97.6 (C1); 82.4 (C34); 56.4 (C9); 53.7 (C17); 49.3 (C20); 43.7 (C15); 40 6 (C13); 39.2 (C5); 10.5 (C39).

MS (FAB): 1001.6 [M+Rb]⁺ c)

17-Allyl-1.14-dihydroxy-12-[2-(4-amino-3-methoxycyclo hexyl)-1-methylvinyl]-23,25-dimethoxy-13,19,21,27-tetra methyl-11-28-dioxa-4-azatricyclo[22.3.1.0⁴,⁹]octacos-18-ene-2.3,10,16-tetraone To a solution of the product of step (b) (35 mg) in acetonitrile (7 ml) was added 40% aqueous hydrofluoric acid (0.5 ml). After stirring for 2.5 hours at room temperature the reaction mixture was poured into ethyl acetate and the separated organic extract was then washed with saturated aqueous sodium hydrogen carbonate solution and brine before being dried (MgSO₄), filtered and evaporated to an oil in vacuo. Column chromatography on silica eluting with hexane/acetone [2:1] then gave the title compound (15 mg) as a foam.

$^{13}$C NMR (CDCl$_3$) δ: (Major rotamer) 212.9 (C16); 196.2 (C2); 169.1 (C10); 164.8 (C3); 139.1 (C19); 135.7 (C41); 132.9 (C29); 128.5 (C31); 122.6 (C18); 116.8 (C42); 97.2 (C1) 82 . 9 (C34) 78 (C12); 75.4 (C23); 73.8 (C25); 73.0 (C2 4); 70.2 (C14); 57.1 (C9); 53.1 (C17); 48.7 (C20); 43.3 (C15); 39.8 (C13); 39.4 (C5); 24.1 (C6); 21.3 (C7); 20.6 (C44); 14.2 (C30); 9.7 (C39).

MS (FAB): 888.5 [M+Rb]+; 826.7 [M+Na]+; 786.7 [M+H-H$_2$O]+

EXAMPLE 63

17-Allyl-1,14-dihydroxy-12-[2-(4-acetamido-3-methoxycyclo
hexyl)-1-methylvinyl1-23-25-dimethoxy-13-19,21,27-tetra
methyl-11,28-dioxa-4-azatricyclo[22.3.1.0$^{4,9}$]octacos-18-ene-2.3,10,16-tetraone a)

17-Allyl-1-hydroxy-12-[2-(4-acetamido-3-methoxycyclo
hexyl)-1-methylvinyl]-23,25-dimethoxy-14-$^t$butyl-dimethyl
silyloxy-13,19,21,27-tetramethyl-11,28-dioxa-4-azatricyclo [22.3.1.0$^{4,9}$]octacos-18-ene-2.3,10,16-tetraone To a solution of the product of Example 62(b) (20 mg) in dry dichloromethane (3 ml) was added pyridine (0.1 ml) and acetyl chloride (0.1 ml). After stirring for 10 minutes at room temperature the reaction mixture was poured into water and this was then extracted with diethyl ether. The organic extract was then washed with dilute aqueous hydrochloric acid and brine before being dried (MgSO$_4$), filtered and evaporated to an oil in vacuo. Chromatography on silica eluting with hexane/acetone [3:1] then gave the subtitle compound (15 mg) as an oil.

b)

17-Allyl-1, 14-dihydroxy-12-[2-(4-acetamido-3-methoxy cyclohexyl)-1-methylvinyl]-23,25-dimethoxy-13,19,21,27-tetra
methyl-11,28-dioxa-4-azatricyclo[22.3.1.0$^{4,9}$]octacos-18-ene-2.3,10,16-tetraone A portion of the product from step (a) (13 mg) was dissolved in acetonitrile (4 ml) and to this was added 40% aqueous hydrofluoric acid (0.1 ml). After stirring for 2 hours at room temperature the reaction mixture was poured into ethyl acetate and the separated organic extract was then washed with water, saturated aqueous sodium hydrogen carbonate solution and brine before being dried (MgSO$_4$), filtered and evaporated to an oil in vacuo. Column chromatography on silica eluting with hexane/acetone [2:1] then gave the title compound (8 mg) as a foam.

$^{13}$C NMR (CDCl$_3$) δ: (Major rotamer) 212.4 (C16); 196.2 (C2); 169 (C10); 164.7 (C3); 139 (C19); 135.5 (C41); 122.4 (C18); 116.7 (C42); 97 (C1); 9.4 (C39)

$^1$H NMR (CDCl$_3$) δ: 2.01 [3H,s,NHCOCH$_3$]
MS (FAB): 930.5 [M+Rb]+; 868.9 [M+Na]+

EXAMPLE 64

17-Allyl-1,14-dihydroxy-12-[2-(4-formyloxy-3-methoxycyclo
hexyl)-1-methylvinyl1-23,25-dimethoxy-13.19,21,27-tetra
methyl-11,28-dioxa-4-azatricyclo[22.3.1.0$^{4,9}$]octacos-18-ene-2.3,10,16-tetraone To a solution of the compound of Example 39(c) (1.103 g) in dry DMF (20 ml) was added sodium azide (2.58 g). After stirring for 2 hours at room temperature the reaction mixture was poured into water and this was then extracted with ethyl acetate. The organic extract after washing with brine was dried (MgSO$_4$), filtered and concentrated to an oil in vacuo. Chromatography on silica eluting with hexane/acetone [3:1] then gave 17-allyl-1-hydroxy-12-(2-(4-formyloxy-3-methoxycyclohexyl)-1-methylvinyl)-23,25-dimethoxy-14-$^t$butyl-dimethylsilyloxy-13,19,21,27-tetra methyl-11,28-dioxa-4-azatricyclo[22.3.1.0$^{4,9}$]octacos-18-ene-2,3,10,16-tetraone (115 mg) as a foam. A portion of this (71 mg) was dissolved in acetonitrile (14 ml) and to this was added 40% aqueous hydrofluoric acid (0.5 ml). After stirring for 3.5 hours at room temperature the reaction mixture was poured into ethyl acetate and the separated organic extract was then washed with water, saturated aqueous sodium hydrogen carbonate solution and brine before being dried (MgSO$_4$), filtered and evaporated in vacuo to an oil. Column chromatography on silica eluting with hexane/acetone [2:1] then gave the title compound (19 mg) as a foam.

$^{13}$C NMR (CDCl$_3$) δ: (Major rotamer) 212.7 (C16); 196.2 (C2); 169.2 (C10); 164.8 (C3); 160.6 (OCHO—); 138.9 (C19); 135.5 (C41); 132.4 (C29); 129.5 (C31); 122.4 (C18); 116.6 (C42); 96.9 (C1); 78.7 (C34); 77.3 (C12); 75.1 (C23); 72.8 (C24); 70 (C14); 56.6 (C9); 52.7 (C17); 48.5 (C20); 43 (C15); 39.6 (C13); 39.2 (C5); 28.2 (C8); 26.2 (C21); 24.5 (C6); 21.1 (C7); 20.4 (C44); 14.1 (C30); 9.3 (C39).

MS (FAB): 916.2 [M+Rb]+; 854.5 [M+Na]+; 832.6 [M+H]+; 814.6 [M+H-H$_2$O]+

EXAMPLE 65

17-Allyl-1,14-dihydroxy-12-[2-(3-oxo-cyclohexyl)-1-methyl
vinyl]-23,25-dimethoxy-13,19,21,27-tetramethyl-11,28-dioxa-4-azatricyclo[22.3.1.0$^{4,9}$]octacos-18-ene-2.3,10,16-tetraone and 17-Allyl-1,14-dihydroxy-12-[2-(3-methoxy-cyclohex-4-enyl)-1-methylvinyl-23,25-dimethoxy-13,19,21,27-tetramethyl-11,28-dioxa-4-azatricyclo[22.3.1.0$^{4,9}$]octacos-18-ene-2.3,10,16-tetraone Silica (220 g, Merck Kieselgel 60, Art. 15111) was added to a solution of the compound of Example 39(c) (250 ml). Volatiles were then removed in vacuo at room temperature and the resulting freely flowing powder was stored at 8° C. for 16 hours. The support was then washed with ethyl acetate and 10% acetone in ethyl acetate containing 2,6-dimethylpyridine. The combined organic extracts after washing with saturated aqueous sodium hydrogen carbonate solution, dilute aqueous hydrochloric acid (1N), saturated aqueous sodium hydrogen carbonate solution and brine were dried, (MgSO$_4$), filtered and concentrated to an oil in vacuo. Chromatography on silica eluting with hexane in an acetone gradient then gave the compound of Example 39(d) (1.12 g) as a foam. Further elution then gave the compound of Example 8(c) (0.5 g) as a foam.

Mixed fractions were then combined, treated with 40% aqueous hydrofluoric acid as above, and re-chromatographed on silica eluting with ethyl acetate to give the first title compound (200 mg).

13C NMR (CDCl$_3$) δ: (Major rotamer) 212.5 (C16); 210.7 (C34); 196.2 (C2); 169 (C10); 164.7 (C3); 139 (C19); 135.5 (C41); 133.1 (C29); 129 (C31); 122.5 (C18); 116.7 (C42); 97.1 (C1); 77.6 (C12); 75.2 (C2.3); 73.7 (C25); 72.8 (C 24); 69.9 (C14); 56.3 (C9); 52.9 (C17); 48.6 (C20); 47.6 (C33); 43.5 (C15); 41.2 (C35); 39.7 (C13); 37.9 (C32); 26.2 (C21); 25.8 (C8); 24.5 (C6); 21.1 (C7); 20.4 (C44); 13.8 (C30); 9.7 (C39).

MS (FAB): 856 [M+Rb]$^+$; 794 [M+Na]$^+$; 736 [M+H-2H$_2$O]$^+$

Further elution then gave the second title compound.

13 NMR (CDCl$_3$): δ(Major rotamer) 212.6 (C16); 196.2 (C2); 168.9 (C10); 164.6 (C3); 139.7 (C19); 135.5 (C41); 132.3 (C29); 129.9 (C31); 122.3 (C18); 116.5 (C42); 128.5 (C35); 128.1 (C36); 96.9 (C1); 73.5 (C25); 72.7 (C24); 70.5 (C14); 56.5 (C9); 52.7 (C17); 48.4 (C20); 27.6 (C8); 26.1 (C21); 24.4 (C6); 21 (C7); 20.3 (C44); 14 (C30); 9.3 (C39).

MS (FAB): 870 [M+Rb]$^+$; 808 [M+Na]$^+$

EXAMPLE 66

17-Allyl-1,14-dihydroxy-12-[2-(cyclopentyl-3-carboxylic acid morpholine amide)-1-methylvinyl]-23.25-dimethoxy -13,19,21,27-tetramethyl-11,28-dioxa-4-azatricyclo [22.3.1.0$^{4,9}$]octacos-18-ene-2.3,10,16-tetraone To a solution of the product of Example 13 was added morpholine (0.03 ml) followed by triethylamine (0.03 ml) and 2-chloro-1-methylpyridinium tosylate (70 mg). After stirring for 1 hour at room temperature a further portion of the tosylate (40 mg) was added and stirring was continued for 5.5 hours at room temperature. Additional triethylamine (0.03 ml) and morpholine (0.03 ml) was then added and the reaction mixture was stirred overnight at room temperature. The reaction was then quenched with dilute aqueous hydrochloric acid (2M, 10 ml) and the mixture was extracted with ethyl acetate. The organic extracts were then washed with saturated aqueous sodium hydrogen carbonate solution and brine before being dried (MgSO$_4$), filtered and evaporated to an oil in vacuo. Chromatography on silica eluting with hexane in an increasing acetone gradient then gave the title compound (30 mg) as a foam.

MS (FAB): 941.4 [M+Rb]$^+$; 880.2 [M+Na]$^+$; 858.4 [M+H]$^+$; 840.4 [M+H-H$_2$O]$^+$

13C NMR (CDCl$_3$) δ: (Major rotamer) 212.4 (C16); 196.2 (C2); 174.6 (cyclopentylCO); 169.1 (C10); 164.7 (C3); 138.9 (C19); 135.6 (C40); 132.5 (C29); 131.3 (C31); 122.7 (C18); 116.7 (C41); 97.1 (C1); 70.0 (C14); 67 and 66.8 (morpholine CH$_2$O); 56.3 (C9); 52.9 (C17); 48.8 (C20); 46.1 and 42.3 (morpholineCH$_2$N); 27.8 (C8); 26.2 (C21); 24.5 (C6); 21.0 (C7); 20.3 (C43); 14.1 (C30); 9.9 (C38)

We claim:
1. A compound of formula I,

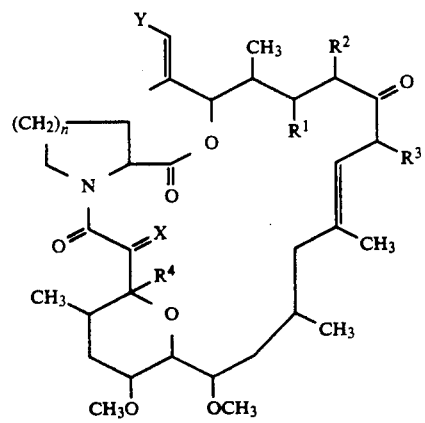

wherein
R$^1$ represents H, OH or C$_{1-10}$ alkoxy;
R$^2$ represents H;
in addition, R$^1$ and R$^2$ may together represent a second bond between the carbon atoms to which they are attached;
R$^3$ represents methyl, ethyl, propyl or allyl;
R$^4$ represents H, OH, C$_{1-10}$ alkyl, C$_{1-10}$ alkoxy, halogen, amino, S-C$_{1-10}$ alkyl, NHCHO or NHCO-C$_{1-10}$ alkyl;
n represents 1 or 2;
X represents O, (H,OH), (H,H) or =NH; and
Y represents a cyclic group of formula II,

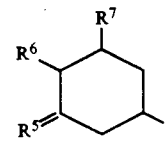

in which R$^5$ represents (H,H), (H,OH), (H, methoxy) or O;
R$^6$ represents H, (R)—OH, (S)—OH, C$_{1-10}$ alkoxy, amino, C$_{1-10}$ alkylamino, C$_{1-10}$ alkanoylamino, formyloxy or halogen;
R$^7$ represents H;
and in addition R$^5$ and R$^6$ may together represent a second bond between the carbon atoms to which they are attached; or R$^6$ and R$^7$ may together represent a second bond between the carbon atoms to which they are attached;
or a cyclic group of formula III,

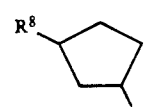

in which R$^8$ represents C$_{1-10}$ alkyl substituted by one or more groups selected from OH, C$_{1-10}$ alkoxy, =O, and CO$_2$H; or C$_{2-10}$ alkenyl optionally substituted by one or more groups selected from OH, =O, or CO$_2$H;
provided that
(a) when n represents 1; R$^1$ represents OH; R$^3$ represents allyl; R$^4$ represents OH; R$^5$ represents (H, methoxy); and R$^6$ represents (R)—OH; then X does not represent O;
(b) when n represents 2;

(i) $R^1$ represents OH; $R^3$ represents methyl, ethyl, allyl or propyl; $R^4$ represents OH; $R^5$ represents (H,methoxy); and $R^6$ represents (R)—OH; then X does not represent O;

(ii) when $R^1$ and $R^2$ together represent a second bond between the carbon atoms to which they ar attached or each represents H; $R^3$ represents allyl or propyl; $R^4$ represents OH; $R^5$ represents (H,methoxy); and $R^6$ represents (R)—OH; then X does not represent O;

(iii) when $R^1$ represents OH, methoxy or together with $R^2$ a second bond between the carbon atoms to which they are attached; $R^3$ represents allyl; $R^4$ represents OH; $R^5$ represents (H,methoxy); and $R^6$ represents methoxy; then X does not represent O;

(iv) when $R^1$ represents H or OH; $R^3$ represents allyl; $R^4$ represents OH; $R^5$ represents (H,methoxy); and $R^6$ represents (R)—OH; then X does not represent (H,OH);

(v) when $R^1$ represents H; $R^3$ represents propyl; $R^4$ represents OH; $R^5$ represents (H,OH); and $R^6$ represents (R)—OH; then X does not represent O;

(vi) when $R^1$ represents OH; $R^3$ represents ethyl; $R^4$ represents OH; $R^5$ represents (H,methoxy); and $R^6$ represents (R)—OH; then X does not represent (H,OH);

(vii) when $R^1$ and $R^2$ together represent a second bond between the carbon atoms to which they are attached or each represents H; $R^3$ represents ethyl; $R^4$ represents OH; $R^5$ represents (H,methoxy); and $R^6$ represents (R)—OH; then X does not represent O;

(viii) when $R^1$ represents OH; $R^3$ represents allyl; $R^4$ represents OH; $R^5$ represents (H,OH); or (H,methoxy); and $R^6$ represents (R)—OH; then X does not represent (H,H);

(ix) when $R^1$ represents OH; $R^3$ represents ethyl; $R^4$ represents OH; $R^5$ represents (H,methoxy); and $R^6$ represents (R)—OH; then X does not represent (H,H);

(x) when $R^1$ represents OH; $R^3$ represents methyl, ethyl or allyl; $R^4$ represents OH; $R^5$ represents (H,OH); and $R^6$ represents (R)—OH; then X does not represent O; and (xi) when $R^1$ represents OH; $R^3$ represents allyl; $R^4$ represents OH; $R^5$ represents O; and $R^6$ represents (R)—OH; then X does not represent O;

and pharmaceutically acceptable esters comprising a $C_{1-6}$ alcohol moiety, amides comprising a $C_{0-6}$ amine moiety, and salts thereof.

2. A compound of formula I, as claimed in claim 1, wherein $R^1$ represents H or OH.

3. A compound of formula I, as claimed in claim 1, wherein $R^4$ represents H, OH, $C_{1-10}$ alkyl, halogen or amino.

4. A compound of formula I, as claimed in claim 1, wherein $R^5$ represents (H,OH) or (H,methoxy).

5. A compound of formula I, as claimed in claim 1, wherein $R^6$ represents H, (R)—OH or amino.

6. A compound of formula I, as claimed in claim 1, wherein $R^8$ represents an amide of a $CO_2H$ group, or $C_{1-10}$ alkyl substituted by $C_{1-10}$ alkoxy.

7. A compound of formula I, as claimed in claim 1, which is 17-allyl-1,14-dihydroxy-12-[2-(3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-allyl-1,14-dihydroxy-12-[2-(cyclopentyl-3-carboxylic acid morpholine amide)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-allyl-14-hydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-allyl-14-hydroxy-12-[2-(4-hydroxy-3-methoxycyclohexyl)-1-methylvinyl]-23,25-dimethoxy-1,13,19,21,27-pentamethyl-11,28-dioxa-4-azatricyclo[22.3.1.0$^{4,9}$]octacos-18-ene-2,3,10,16-tetraone;

17-allyl-1-amino-14-hydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-allyl-1-fluoro-14-hydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-allyl-1, 14-dihydroxy-12-[2-(cyclopentyl-3-methanol(methylether))-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; or 17-allyl-1, 14-dihydroxy-12-[2-(4-amino-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

8. A pharmaceutical composition comprising a compound of formula I, as defined in claim 1, in association with a pharmaceutically acceptable adjuvant, diluent or carrier.

9. A method of effecting immunosuppression which comprises administering a therapeutically effective amount of a compound of formula I, as defined in claim 1, to a patient.

* * * * *

Adverse Decisions in Interference

Patent No. 5,296,489, David K. Donald, Mark Furber, Martin E. Cooper, IMMUNO SUPPRESSIVE MACROCYCLIC COMPOUNDS, Interference No. 103,831, final judgment adverse to patentees rendered November 19, 1997, as to claims 1-9.

*(Official Gazette April 21, 1998)*